United States Patent
Coady et al.

(10) Patent No.: US 9,084,735 B2
(45) Date of Patent: Jul. 21, 2015

(54) SELF-ASSEMBLING BIS-UREA COMPOUNDS FOR DRUG DELIVERY

(71) Applicants: International Business Machines Corporation, Armonk, NY (US); Agency For Science, Technology and Research, Singapore (SG)

(72) Inventors: Daniel J. Coady, San Jose, CA (US); Richard A. Dipietro, Campbell, CA (US); Amanda C. Engler, San Jose, CA (US); James L. Hedrick, Pleasanton, CA (US); Shao Qiong Liu, Singapore (SG); Jed W. Pitera, Portola Valley, CA (US); Shrinivas Venkataraman, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 13/956,821

(22) Filed: Aug. 1, 2013

(65) Prior Publication Data

US 2015/0037390 A1 Feb. 5, 2015

(51) Int. Cl.
| | |
|---|---|
| *A61K 9/70* | (2006.01) |
| *A61K 31/43* | (2006.01) |
| *A61K 31/431* | (2006.01) |
| *A61K 31/616* | (2006.01) |
| *A61K 31/166* | (2006.01) |
| *A61K 31/17* | (2006.01) |

(52) U.S. Cl.
CPC . *A61K 9/70* (2013.01); *A61K 31/43* (2013.01); *A61K 31/431* (2013.01); *A61K 31/616* (2013.01); *A61K 31/166* (2013.01); *A61K 31/17* (2013.01)

(58) Field of Classification Search
None
See application file for complete search history.

(56) References Cited

U.S. PATENT DOCUMENTS

| 4,617,186 A | 10/1986 | Schafer et al. |
|---|---|---|
| 7,435,852 B2 | 10/2008 | Levon et al. |
| 2007/0110709 A1 | 5/2007 | Ranger et al. |
| 2007/0243255 A1 | 10/2007 | Xu et al. |

(Continued)

FOREIGN PATENT DOCUMENTS

| FR | 2930777 A1 | 11/2009 |
|---|---|---|
| WO | 2009061473 A2 | 5/2009 |

(Continued)

OTHER PUBLICATIONS

Ghanem et al., "Covalent modification of glassy carbon surface with organic redox probes through diamine linkers using electrochemical and solid-phase synthesis methodologies," J. Mater. Chem., 2008, 18, 4917-4927; First published as Advance Article on the web Sep. 17, 2008.

(Continued)

*Primary Examiner* — Bethany Barham
*Assistant Examiner* — Barbara Frazier
(74) *Attorney, Agent, or Firm* — Michael R. Roberts

(57) ABSTRACT

Cationic, anionic, and/or zwitterionic bis-urea compounds self-assemble by non-covalent interactions in aqueous solution to form high aspect ratio nanofibers. The nanofibers reversibly bind drugs by non-covalent interactions, forming drug compositions for exhibiting sustained release of the drug.

12 Claims, 9 Drawing Sheets

(56) References Cited

U.S. PATENT DOCUMENTS

| | | |
|---|---|---|
| 2009/0156459 A1 | 6/2009 | Castillo et al. |
| 2011/0059280 A1 | 3/2011 | Montarnal et al. |
| 2013/0281515 A1 | 10/2013 | Coady et al. |

FOREIGN PATENT DOCUMENTS

| | | |
|---|---|---|
| WO | 2009141558 A2 | 11/2009 |
| WO | 2011123061 A1 | 10/2011 |

OTHER PUBLICATIONS

Giacomelli, et al., "Specific Interactions Improve the Loading Capacity of Block Copolymer Micelles in Aqueous Media," Langmuir 2007, 23, 6947-6955; Published on Web May 25, 2007.

Pittelkow, et al., "Mono Carbamate Protection of Aliphatic Diamines Using Alkyl Phenyl Carbonates," Organic Syntheses, vol. 84, p. 209-214 (2007); Coll. vol. 11, p. 942-946 (2009).

Gong, et al., Biochemical and Biophysical Research Communications 240, 557-560 (1997).

USPTO, U.S. Appl. No. 13/449,643, filed Apr. 18, 2012 to Coady, et al., Non-Final Office Action mailed Jun. 5, 2014.

Deaton, Kimberley R., "Low Molecular Weight Bis-Urea Organogelators", Feb. 21, 2002, copyright Kimberley R. Deaton 2002, downloaded from the web at "http://www.chemistry.illinois.edu/research/organic/seminar_extracts/2001_2002/s02_Deaton.pdf" on Jan. 26, 2015.

Esch, et al., "Self-Assembly of Bisurea Compounds in Organic Solvents and on Solid Substrates", Chemistry—A European Journal, vol. 3, Issue 8, pp. 1238-1243, ABSTRACT, Aug. 1997.

Lankalapalli, et al., "Polyelectrolyte Complexes: A Review of their Applicability in Drug Delivery Technology," Indian J Pharm Sci. Sep.-Oct. 2009; 71(5): 481-487.

Liechty, et al.,"Polymers for Drug Delivery Systems", Annu Rev Chem Biomol Eng. 2010 ; 1: 149-173.

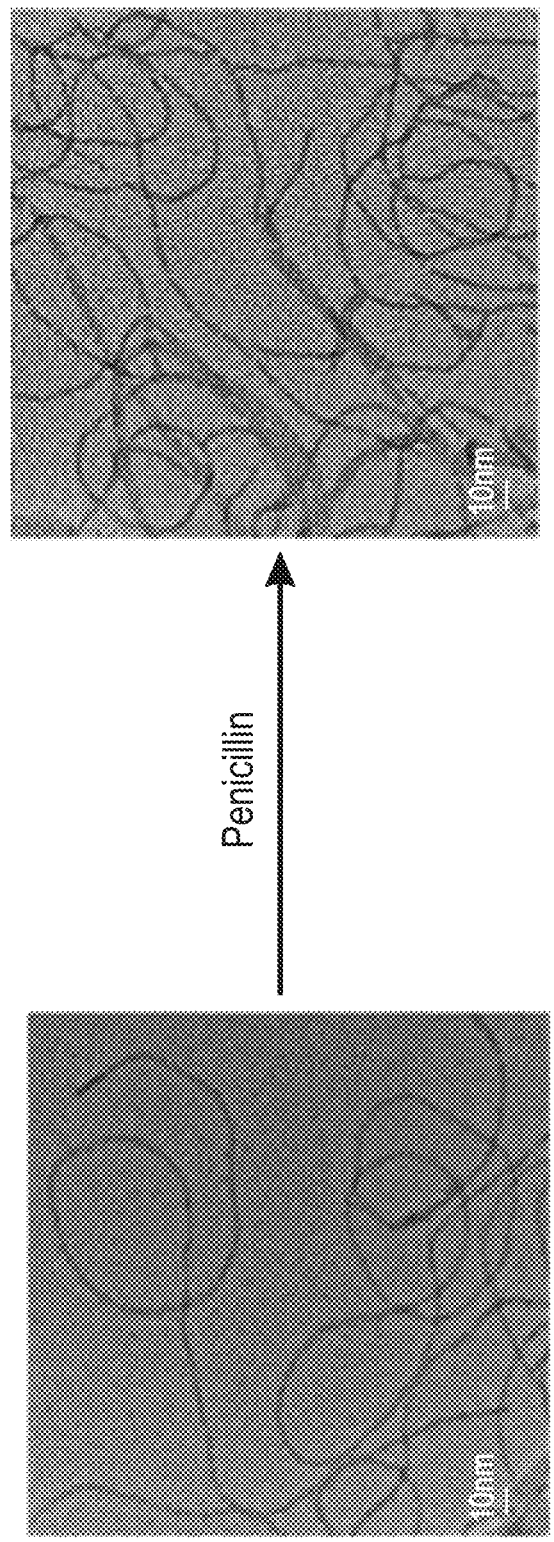

SELF-ASSEMBLING BIS-UREA COMPOUNDS FOR DRUG DELIVERY

PARTIES TO A JOINT RESEARCH AGREEMENT

This invention was made under a joint research agreement between International Business Machines Corporation and the Agency For Science, Technology and Research.

BACKGROUND

The present invention relates to fibers for encapsulating and delivering drugs, and more specifically, to cationic fibers formed by self-assembly of cationic compounds for reversible binding and controlled release of hydrophobic anionic drugs.

The majority of clinically used drugs are low molecular weight compounds that are characterized by short half-life in the blood stream, high clearance rate, limited solubility, limited stability, and/or high toxicity. A number of drug delivery systems have been proposed to overcome one or more of these drawbacks including liposomes, microspheres, virosomes, nanocrystals, nanotubes and electrospinning. For example, when treating cancerous tumors, efficient drug delivery requires novel nanocarriers that have a hydrophilic shell to prevent protein adsorption, thereby prolonging blood circulation, and a hydrophobic core for loading (typically hydrophobic or moderately polar) drugs. Nanosize allows passive targeting into tumor tissue based on the enhanced permeability and retention (EPR) effect. Ideal nanocarriers should possess one or more, and preferably all, of the following properties: 1) biodegradability and biocompatibility; 2) high loading capacity for various drugs; 3) kinetic stability after injection into the blood stream; 4) narrow size distribution for desirable and uniform biodistribution, and 5) biological ligands for active targeting to tumor tissues.

Polymer therapeutics includes polymer/drug complexes (in which the polymer acts as a sequestrant for the drug), covalently bound polymer-drug conjugates, covalently bound polymer-protein conjugates, non-covalently bound polymer-DNA complexes (polyplexes), and polymeric micelles to which drugs are covalently bound and/or physically incorporated. Conventionally, nanoscale therapeutics are derived from polymer-drug (or polymer-protein) conjugates, in which a drug is covalently linked to a polymer through a cleavable linker such as a lysosome-dependent Gly-Phe-Leu-Gly tetrapeptide and pH sensitive cis-aconityl, hydrazone, or acetal linkages. Alternatively, supramolecular drug delivery systems are based on the assembly of block copolymer into micelles and partitioning of drug into the micelle interior. Dendritic polymer nanocarriers also show promise for tumor targeting and drug delivery. Both covalent and non-covalent systems can utilize the enhanced permeability and retention effect in disorganized and leaky angiogenic tumor vasculature for targeting.

Self-assembled block copolymer micelles are typically several tens of nanometers in diameter with a relatively narrow size distribution and have long been explored because they are expected to be a simple, economic and a versatile approach to nanosized drug carriers. The major obstacles for supramolecular drug-delivery systems based on non-covalent entrapment of drugs into core-shell architectures are the lack of kinetic stability of polymer micelles that are susceptible to infinite dilution arising from their administration and poor drug loading capacity. Critical micelle concentration (CMC) of polymers is an important parameter to anticipate in vivo kinetic stability of the micelles. Efforts to bolster the weak intermolecular interactions that effect micelle formation and stability include selective crosslinking of either the interior (core) or exterior (corona), crosslinking throughout the micelle, and/or stabilizing non-covalent interactions. Despite the improved stability of the chemical cross-linking, this approach may not be optimal for the encapsulation of a guest molecule or for biodegradability. The precisely-tunable structure of block copolymers combined with new synthetic methodologies can allow the use of non-covalent interactions in polymeric assemblies. The role of non-covalent interactions is particularly pronounced as a collective driving force to the formation of stable aggregates as well as micelle-drug interactions. For example, Giacomelli, et al., Langmuir 2007, volume 23, pages 6947-6955 reported that specific acid-base interaction between hydrophobic drug molecules ($R^1$—COOH) and polymer segments ($H_2N$—$R^2$) improved the drug loading capacity of block copolymer micelles.

Another class of drug delivery macromolecules with well-defined architecture is branched polymers including dendrimers and hyperbranched polymers. Dendrimer structure was first reported in the 1980s. The unique architecture of dendrimers offers advantages including presentation of high local concentration of desired functionality (such as positive charges, targeting groups, and hydrophilic groups for water solubility) on the periphery of the molecules. This core/shell structure serves as the main principle of their drug sequestration either by physical or chemical attachment. Dendrimers are often synthesized either by divergent growth from the initiator core to the targeted generation, or from the periphery inward, terminating at the core, known as the convergent method. While the divergent method normally produces dendrimers with symmetrical architecture, the convergent method allows one to synthesize dendrimers with different dendritic segments or layers of functionalities. The most commonly studied dendrimers for medical applications include polyamidoamine (PAMAM), polypropyleneimine (PPI), dendrimers and hyperbranched polymers derived from bis(hydroxymethyl)propionic acid, carbosilane dendrimer, and branched-peptides or dendritic peptides from an L-lysine core.

A key advantage of dendrimers over a polymeric sequestrant or a micelle is the absence of polydispersity in molecular weight. Dendrimers are molecules with exact molecular weights, which from a regulatory point of view, minimizes the complexities associated with polymers. Moreover, the low polydispersity should provide reproducible pharmacokinetic behavior in contrast to a polymer that contains significant distribution in molecular weights. Limitations of dendrimers may include the cost of synthesis, limited cargo space and small size which may allow them to randomly "leak" through the vascular wall. With this in mind, there is a need to devise a strategy to preserve the multivalency associated with dendrimers but increase the particle size. In part this has been accomplished using dendritic-linear or dendritic-star hybrids. Although this accomplishes part of the goal, it reintroduces the issue of molecular weight dispersity.

Therefore, a clear need exists for a drug delivery vehicle that has an exact molecular weight, high multivalency, and the appropriate size and functionality to allow long circulation times.

SUMMARY

Accordingly, a composition of matter is disclosed comprising a bis-urea compound of formula (1):

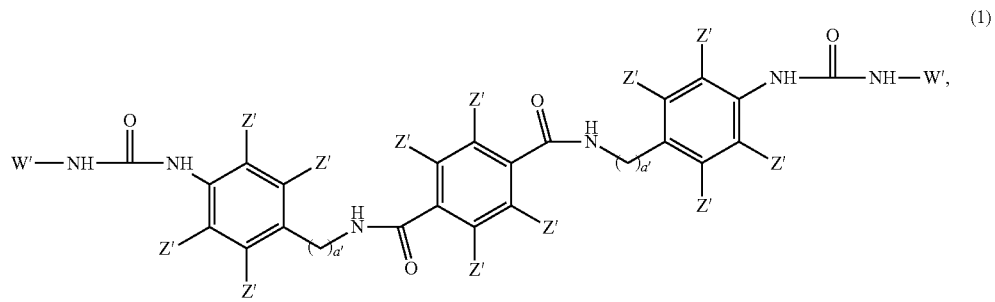

wherein
a' is 0 or 1,
each W' is an independent monovalent radical comprising a cationic group, anionic group, and/or a zwitterionic group, wherein W' comprises 2 to about 25 carbons, and
each Z' is an independent monovalent radical selected from the group consisting of hydrogen, halides, and functional groups comprising 1 to about 6 carbons.

Also disclosed is a drug composition, comprising:
a solvent; and
a drug complex comprising a drug bound by non-covalent interactions to a fiber, wherein i) the fiber has an average diameter of 4 nm to 10 nm, ii) the fiber has an aspect ratio of 100:1 or more, iii) the fiber comprises 3 or more self-assembled molecules of a bis-urea compound bound by non-covalent interactions, and iv) the bis-urea compound has a structure according to formula (1):

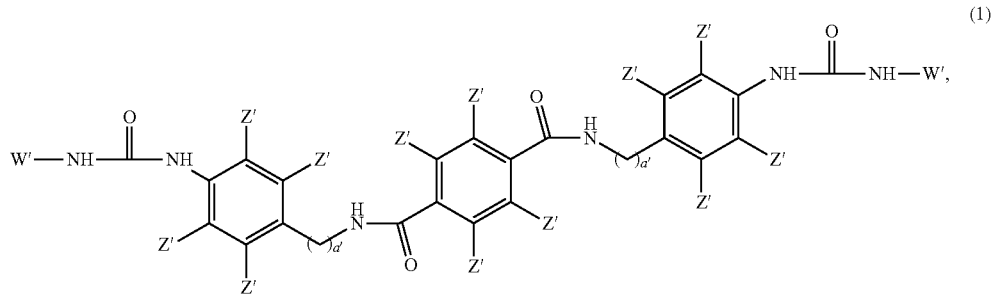

wherein
a' is 0 or 1,
each W' is an independent monovalent radical comprising a cationic group, anionic group, and/or a zwitterionic group, wherein W' comprises 2 to about 25 carbons, and
each Z' is an independent monovalent radical selected from the group consisting of hydrogen, halides, and functional groups comprising 1 to about 6 carbons.

Also disclosed is a method of forming a drug composition, comprising: forming a first mixture comprising a solvent and a bis-urea compound of formula (1):

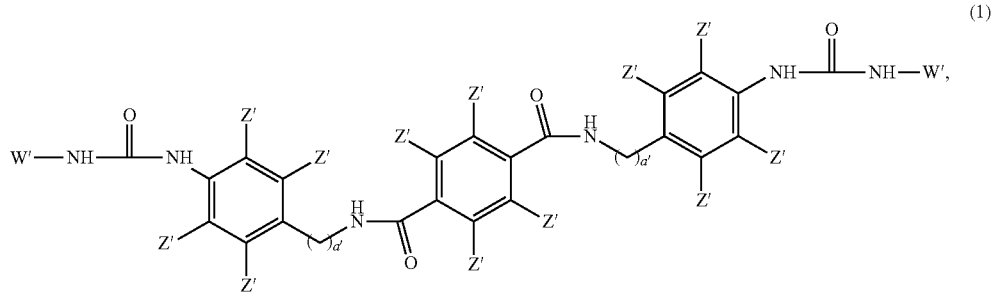

wherein
a' is 0 or 1,
each W' is an independent monovalent radical comprising a cationic group, anionic group, and/or a zwitterionic group, wherein W' comprises 2 to about 25 carbons, and
each Z' is an independent monovalent radical selected from the group consisting of hydrogen, halides, and functional groups comprising 1 to about 6 carbons;

allowing the bis-urea compound of the first mixture to self-assemble, thereby forming a second mixture comprising fibers, wherein i) each of the fibers comprises 3 or more self-assembled molecules of the bis-urea compound bound by non-covalent interactions, and ii) each of the fibers has an aspect ratio of 100:1 or more and an average diameter of 4 nm to 10 nm;

adding a drug to the second mixture, thereby forming the drug composition, wherein the drug composition comprises a complex of the drug and the fibers bound by non-covalent interactions, and the drug composition is suitable for controlled release of the drug.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

shorter lengths, with an average diameter of 4 nm.

FIG. 4 is a set of transmission electron micrographs (TEMs) of blank nanofibers formed by C-4 (left side) and penicillin G loaded nanofibers of C-4 (right side), showing the nanofiber structure is maintained by the loaded nanofiber.

DETAILED DESCRIPTION

The invention is based on the discovery that a bis-urea compound having a triaromatic core can self-assemble in a suitable solvent to produce a high aspect ratio fiber, which comprises two or more molecules of the bis-urea compounds bound by non-covalent interactions. Non-covalent interactions include ionic and/or hydrophobic interactions. The preformed fiber can sequester a drug by non-covalent interactions. The resulting fiber/drug complex (referred to herein for brevity as a "drug complex") can potentially enhance the

Figure 1:
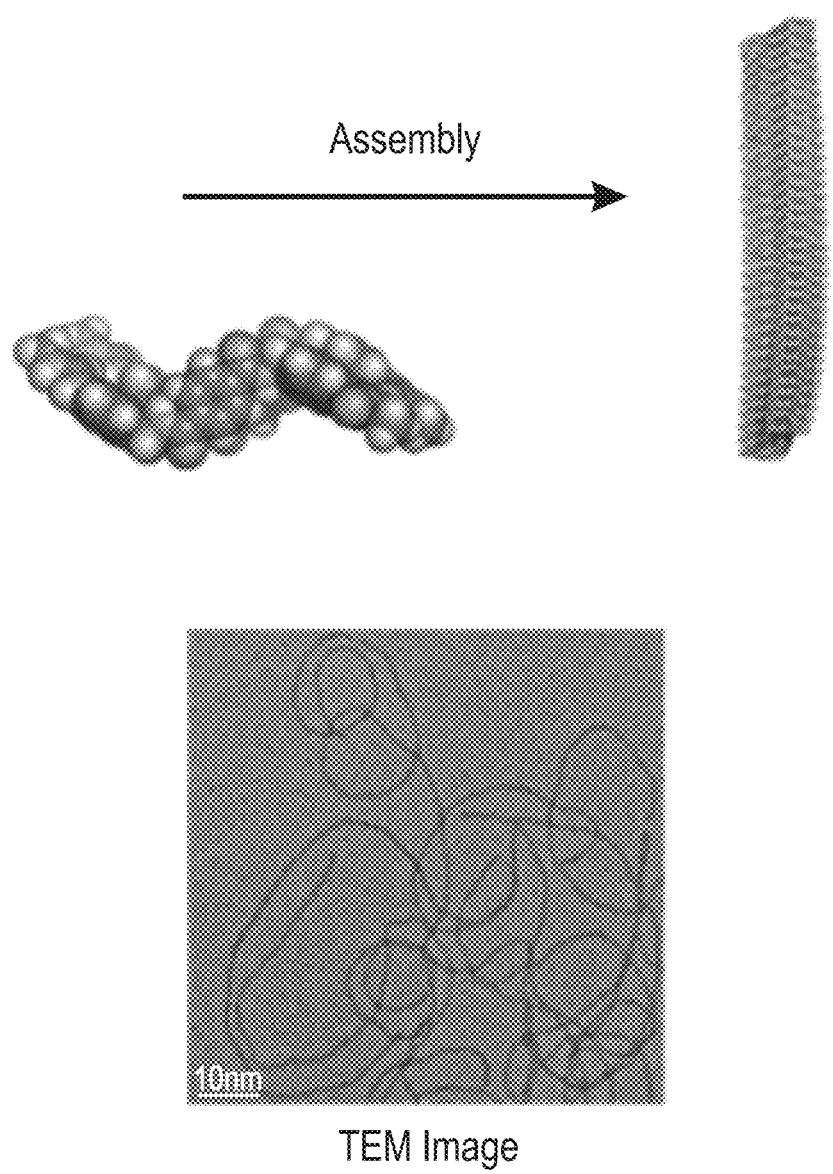
FIG. 1 contains two drawings of the molecular mechanics conformational analysis of a self-assembling terephthalamide bis-urea compound.

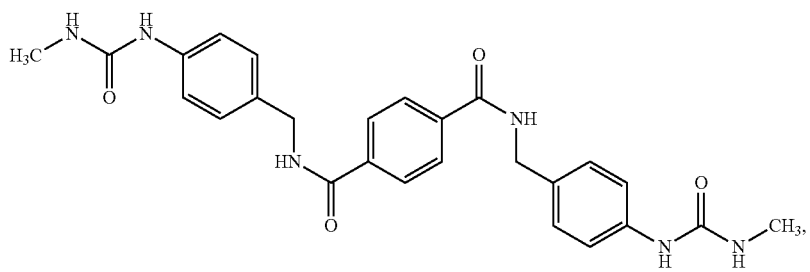 [SMILES: CNC(=O)Nc1ccc(CNC(=O)c2ccc(C(=O)NCc3ccc(NC(=O)NC)cc3)cc2)cc1]

which has a zig-zag or bent structure. The distal benzyl urea groups are perpendicular to the terephthalamide core. These zig-zag structures can pack together into planar sheets stabilized by urea-urea hydrogen bonds and aromatic stacking. The lower drawing is a dimer. The drawing on the right is a nanorod containing about 30 self-assembled molecules of the terephthalamide bis-urea compound. FIG. 1 also contains a transmission electron micrograph (TEM) image of nanofibers formed with bis-urea compound C-4.

Figures 2A, 2B, 2C:
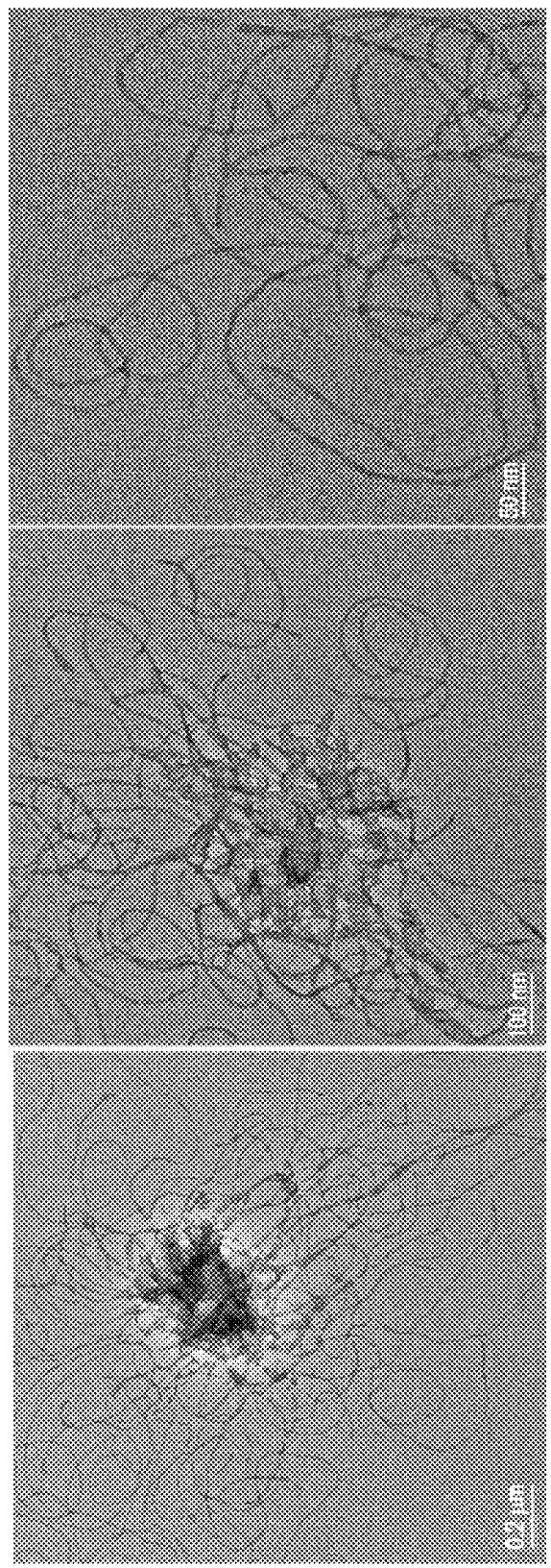

FIGS. 2A to 2C are TEMs of nanofibers formed by C-4 (several hundred nm in length and about 5 nm in diameter) at three magnifications.

Figure 3A:
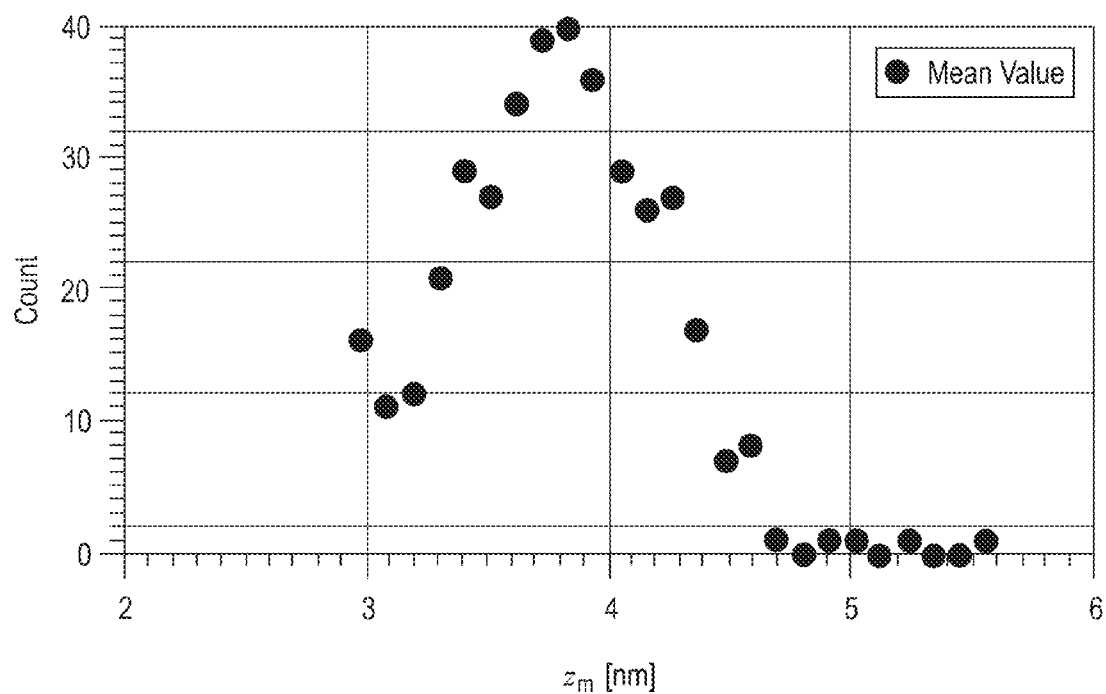
FIG. 3A is the solution AFM.
Figure 3B:
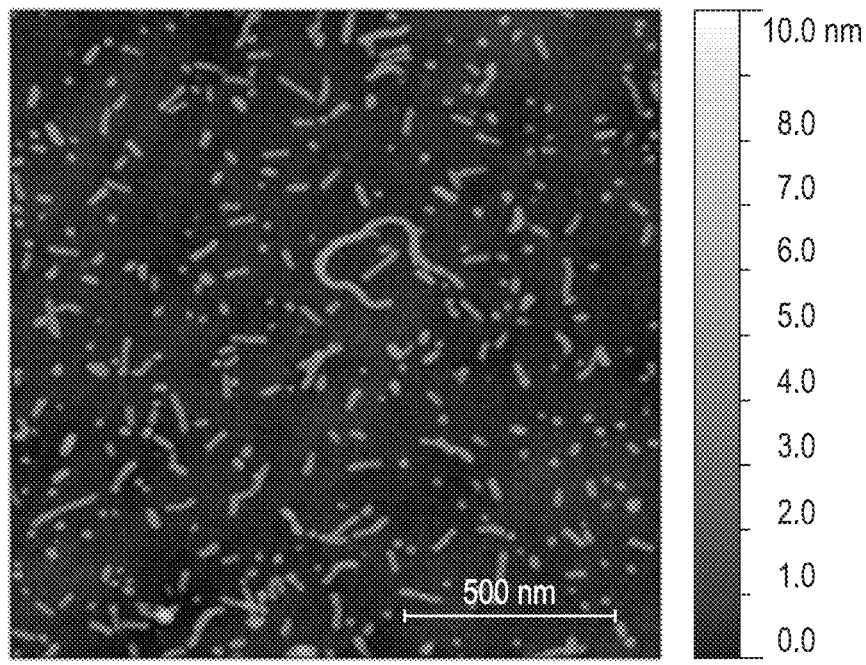
FIGS. 3B and 3C are dry fiber AFMs.
Figure 3C:
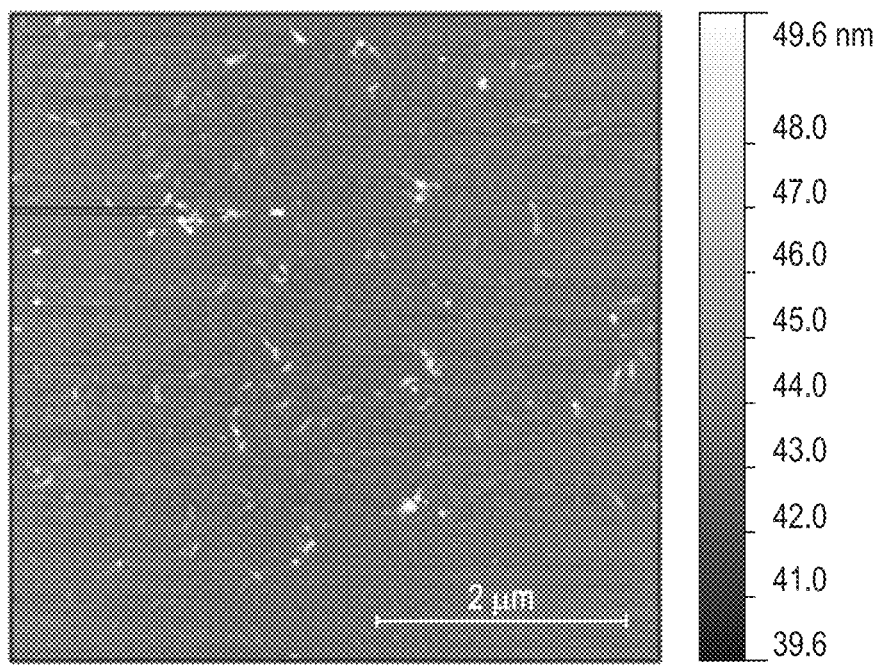

FIGS. 3A to 3C are atomic force microscopy (AFM) images of a film (AFM) prepared from nanofibers of C-4 showing anisotropic structures, although considerably therapeutic effectiveness of the drug by improving the water solubility, macrophage stealthiness, cell targeting, cell penetration capabilities of the drug, and/or by providing sustained release of the drug. The molecular weight of the drug can be higher than the molecular weight of the bis-urea compound used to form the fibers. The self-assembled fibers are reversible. That is, a fiber can dis-assemble in a suitable solvent into separately dissolved molecules of the bis-urea compound.

Unlike a polymer that has a broad spectrum of molecular weights, a bis-urea compound has an exact molecular weight. The bis-urea compounds have structures in accordance with formula (1):

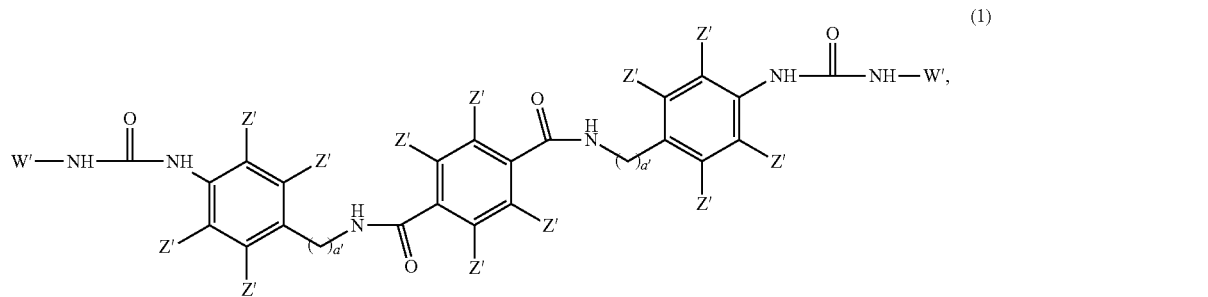
(1)

wherein
a' is 0 or 1,
each W' is an independent monovalent radical comprising a cationic group, anionic group, and/or a zwitterionic group, wherein W' comprises 2 to about 25 carbons, and each Z' is an independent monovalent radical selected from the group consisting of hydrogen, halides, and functional groups comprising 1 to about 6 carbons.

As indicated by formula (1), the bis-urea compounds have a bis-urea core of formula (2):

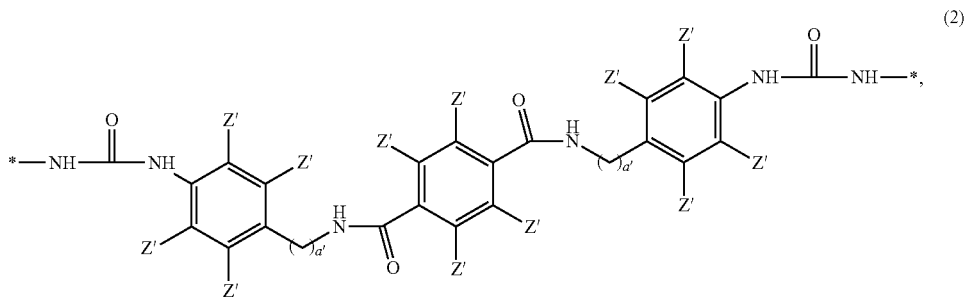
(2)

wherein a' and Z' have the meaning described above, and the starred bonds indicate attachment points to end groups comprising W'.

The bis-urea compounds can be cationic, anionic, or zwitterionic. The self-assembled fibers have a net charge corresponding to the sum of the charges of the assembled molecules of one or more bis-urea compounds used to prepare a fiber. In an embodiment, the bis-urea compound is cationic, and the bis-urea compound self-assembles into high aspect ratio supramolecular cationic fiber in water. Herein, the term "fiber" includes high aspect ratio fibers comprising hundreds of molecules of one or more bis-urea compounds bound by non-covalent interactions in a stack, and low aspect ratio rods comprising about 2 to about 100 molecules of one or more bis-urea compounds bound by non-covalent interactions in a stack.

In a preferred embodiment, each W' of formula (1) comprises a cationic group, and the bis-urea compounds are bis-cationic compounds having the general formula (3):

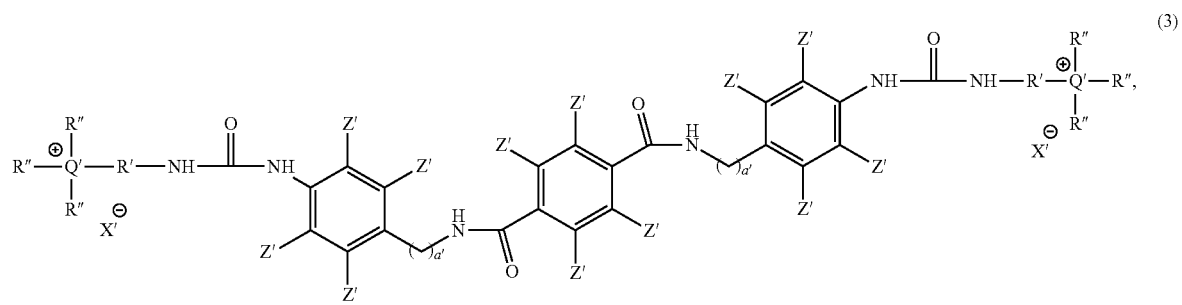

(3)

wherein a' is 0 or 1, each Q' is an independent positive-charged tetravalent heteroatom selected from the group consisting of nitrogen, phosphorous, and combinations thereof, each X' is an independent negative-charged ion, each Z' is an independent monovalent radical selected from the group consisting of hydrogen, halides, and functional groups comprising 1 to about 6 carbons, each R' is an independent divalent linking group comprising at least 1 carbon, each R" is an independent monovalent radical selected from the group consisting of hydrogen and functional groups comprising at least one carbon, and $(R")_3Q'-R'$ comprises 2 to about 25 carbons.

The remainder of the description section is directed to compounds of formula (3). It should be readily apparent to those of skill in the art that the general principles governing self-assembly and drug sequestration can be adapted or applied to bis-urea compounds having neutral, anionic, and/or zwitterionic W' moieties.

When Q' is nitrogen, $(R")_3Q'-R'$ group of the bis-cationic compound formula (3) can be selected from the group consisting of protonated primary amines, protonated secondary amines, protonated tertiary amines, quaternary amines, and combinations thereof When Q' is phosphorous, each R" and R' of an $(R")_3Q'-R'$ group comprises at least one carbon.

Non-limiting exemplary X' include chloride, bromide, iodide, acetate ion, and/or trifluoroacetate. X' can be an anion of a drug. That is, one or both of the X' groups of formula (1) can be an anion of a drug.

Fibers obtained by self-assembly of compounds of formula (3) can form a stable complex with a negative-charged form a drug and/or a zwitterionic drug having a negative-charged group. For simplicity, these drugs are referred to collectively as "anionic drugs." The anionic drug can be present in the drug composition in an amount of more than more than 0 mol % to about 100 mol % based on total moles of the bis-cationic compound. The bis-urea compound:anionic drug mole ratio of the drug composition is preferably about 1:1. Thus, a portion of the anionic species present in the drug composition consists of negative-charged counterions X' (e.g., iodide, bromide, chloride, acetate, trifluoroacetate, and the like) of the bis-urea compound.

Non-limiting examples of self-assembling bis-cationic compounds include:

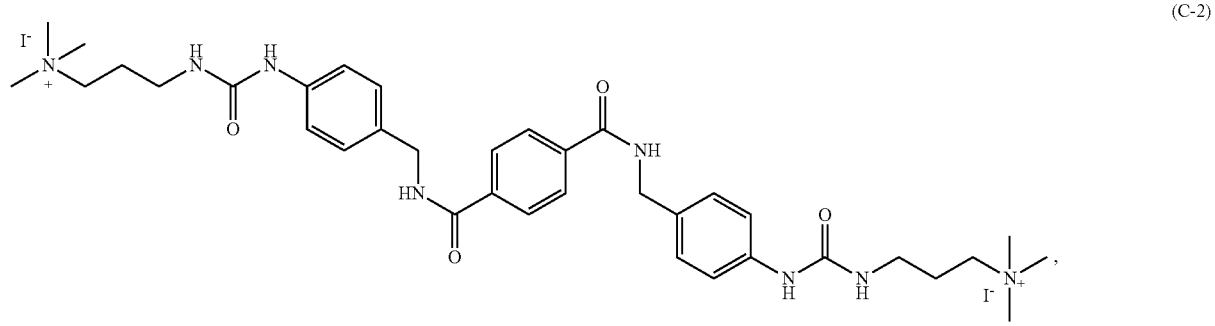

(C-2)

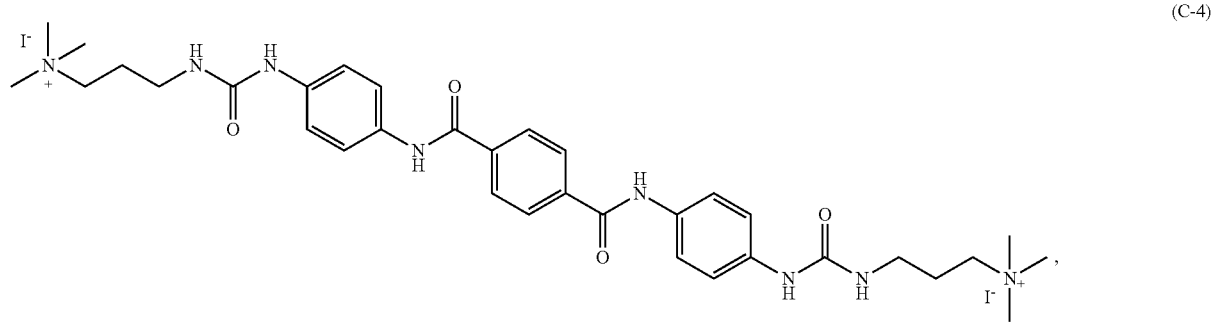

(C-4)

(C-6)
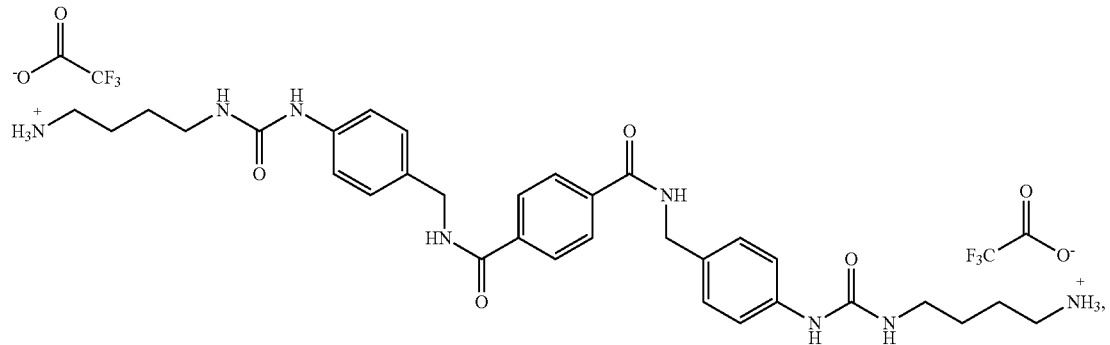
(C-8)
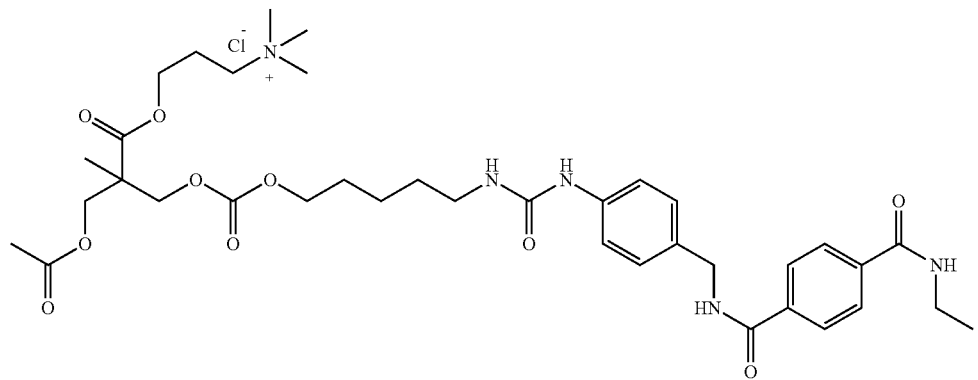
(C-10)
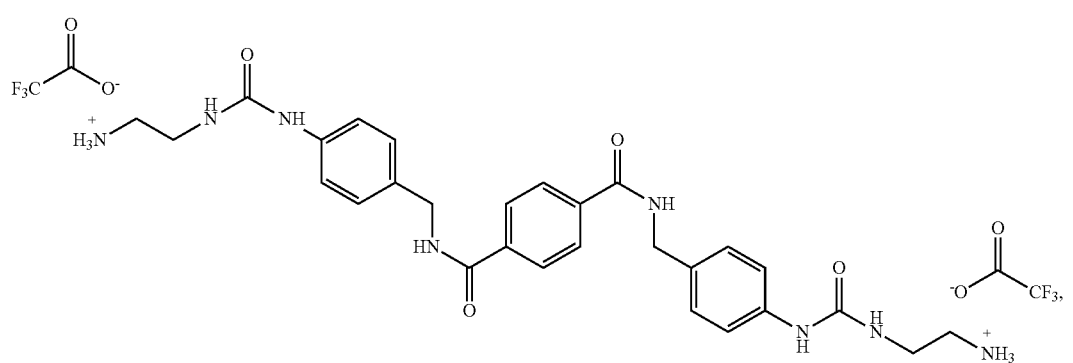

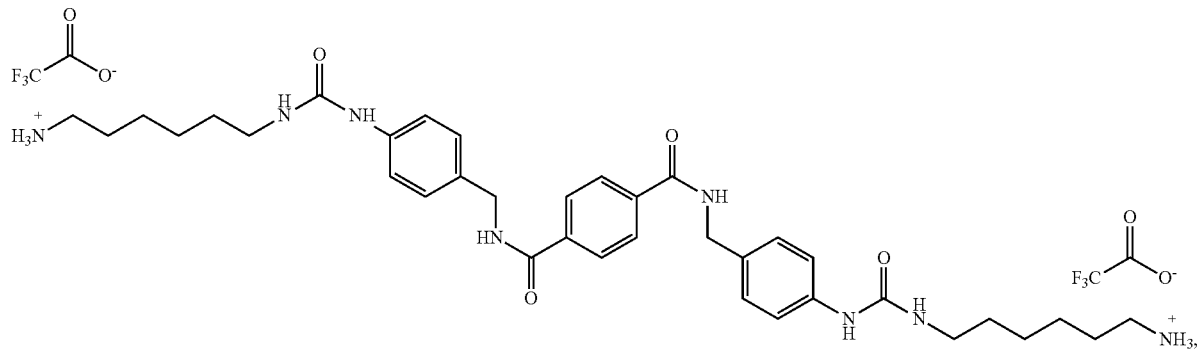

(C-12)

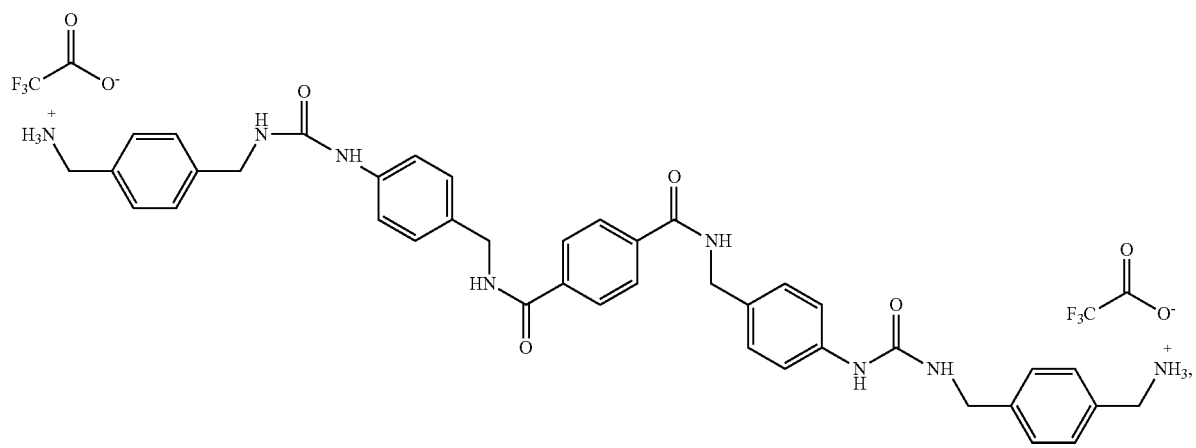

(C-14)

and combinations of the foregoing compounds.

The above bis-cationic compounds self-assemble in aqueous solution to form cationic fibers having polymer-like long-range order and a plurality of cationic surface charges capable of sequestering an anionic drug. The fibers comprise 3 or more molecules of the bis-cationic compound, preferably 100 or more molecules of the bis-cationic compound. Preferably the fibers have an aspect ratio of about 100:1 or more based on the length and diameter of the fiber. The fibers have an average diameter of about 4 nm to about 10 nm.

Molecular mechanics conformational analysis of the bis-urea core structure of formula (2) using the model compound

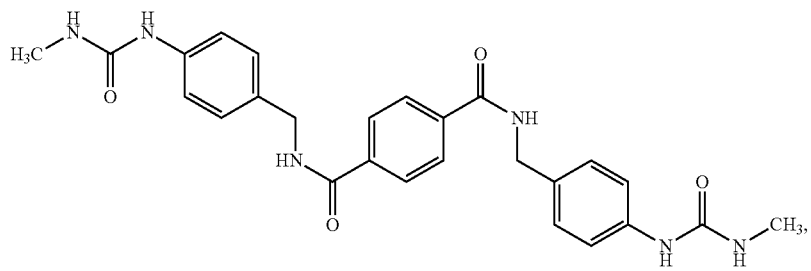 [SMILES: CNC(=O)Nc1ccc(CNC(=O)c2ccc(C(=O)NCc3ccc(NC(=O)NC)cc3)cc2)cc1]

reveals a zig-zag or bent structure in which the distal benzyl urea groups are perpendicular to the central terephthalamide group (FIG. 1, molecular drawing). Because the amide and urea groups are perpendicular to one another, the aromatic rings of the bis-cationic compounds can stack against one another in a layered format stabilized by hydrophobic interactions and intermolecular amide-amide hydrogen bonds, resulting in formation of a dimer (left drawing) and rod-like structure (right drawing) as shown in FIG. 1. The nanosized rods are mechanically stable and are capable of further growth into high aspect ratio fibers. A transmission electron micrograph (TEM) of supermolecular fibers formed from a bis-cationic compound C-4 is also shown in FIG. 1.

A method of preparing a drug composition using the bis-cationic compounds comprises i) forming an aqueous mixture comprising a disclosed bis-cationic compound, ii) allowing the bis-cationic compound to self-assemble in the aqueous mixture, thereby forming a second aqueous mixture comprising cationic fibers comprising a plurality of molecules of self-assembled bis-cationic compound bound by non-covalent interactions, and iii) combining the second aqueous mixture with an anionic drug, thereby forming the drug composition comprising a complex of the fibers and the anionic drug bound by non-covalent interactions. The anionic drug comprises a negative-charged functional group (e.g., carboxylate group) and a positive-charged counterion (e.g., sodium ion, potassium ion, and the like). In an embodiment, the positive-charged counterion is not covalently bonded to the portion of drug structure linked to the negative-charged functional group.

Zwitterionic drugs have a chemical structure comprising i) at least one negative-charged group covalently bound to the medically significant chemical structure of the zwitterionic drug and ii) at least one positive-charged center covalently bound to the medically significant chemical structure of the drug. The negative-charged group of the zwitterionic drug is potentially capable of forming a complex with the cationic fibers for controlled release of the drug.

The anionic drug is preferably combined with pre-formed self-assembled cationic fibers of the bis-cationic compound rather than with the bis-cationic compound prior to self-assembly.

Upon mixing the positive-charged fibers and the anionic drug, a portion of the negative-charged counterion X' of the bis-cationic compound is partially exchanged with the negative-charged drug to form an ionic drug complex. The cationic fiber/anionic drug complex is further stabilized by hydrophobic interactions of the non-charged portion of the anionic drug and cationic fiber structures (e.g., the stacked triaromatic bis-urea portion of the core structure of the fiber interacting with the beta-lactam core of penicillin G). The released negative-charged ion X' (e.g., chloride, bromide, iodide, acetate, trifluoroacetate) can form a salt with an unbound positive-charged counterion of the anionic drug (e.g. sodium ion, potassium ion). If the drug is a zwitterionic drug, then the released X' can form a salt with a covalently bound positive-charged group of the zwitterionic drug. Any unbound salt species (i.e., not covalently bound to the drug and/or the fibers) is considered excess salt (e.g., a potassium or sodium salt of X') that can be removed from the drug composition prior to employing the drug composition in a therapeutic application. Alternatively, the excess salt can be retained in the drug composition.

Exemplary drugs include antibiotics and/or non-steroidal anti-inflammatory drugs (NSAID). Preferably, the drug has a carboxyl group and/or a sulfonic acid group that can be deprotonated to produce an anionic form of the drug having a negative-charged carboxylate group and/or a sulfonate group associated with a positive-charged counterion (e.g., potassium ion or sodium ion).

Exemplary antibiotics include penicillins of formula (4):

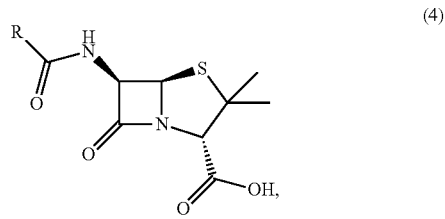

wherein R is a monovalent radical comprising 1 or more carbons. Non-limiting examples of penicillins include:

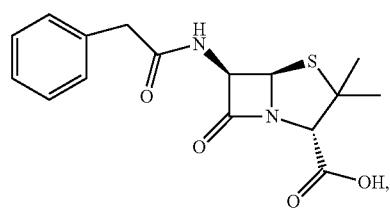

(penicillin G, or penG)

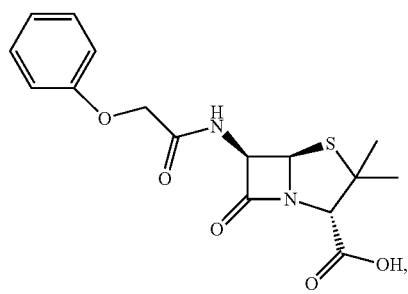

(penicillin V)

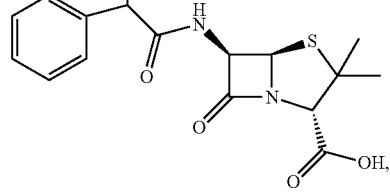

(ampicillin)

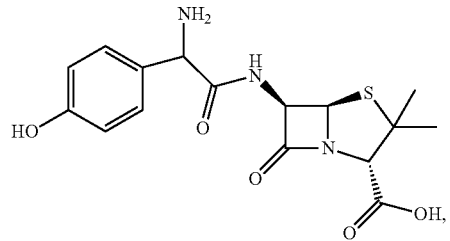

(amoxicillin)

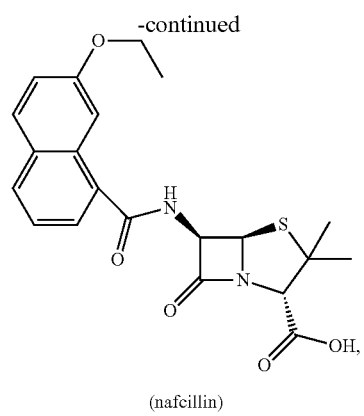
(nafcillin)

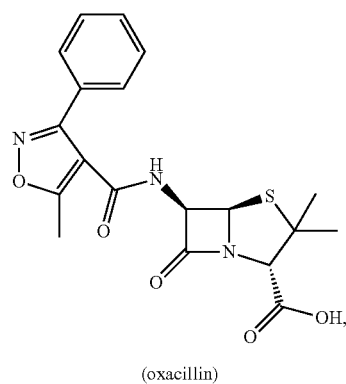
(oxacillin)

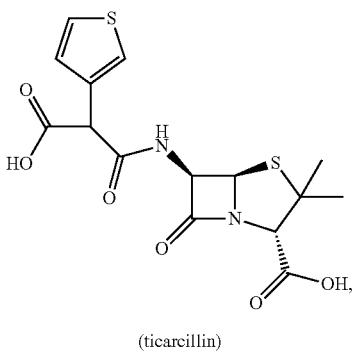
(ticarcillin)

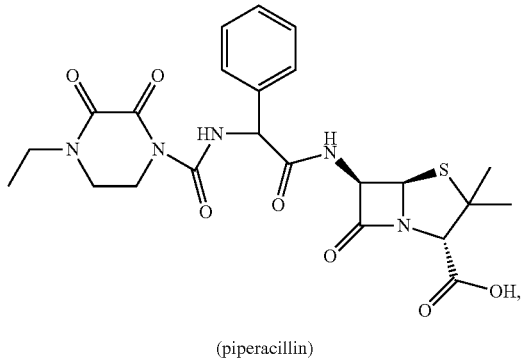
(piperacillin)

deprotonated forms of any of the foregoing compounds (e.g., sodium and/or potassium salts of the carboxyl group of the drug), and combinations thereof.

Other antibiotics include cephalosporins of general formula (5):

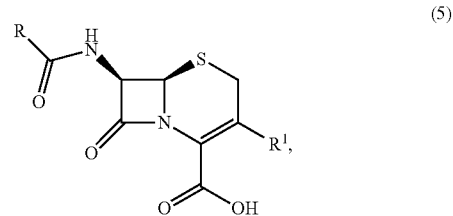

(5)

wherein R and $R^1$ are monovalent radicals comprising at least one carbon. Non-limiting examples of cephalosporins include:

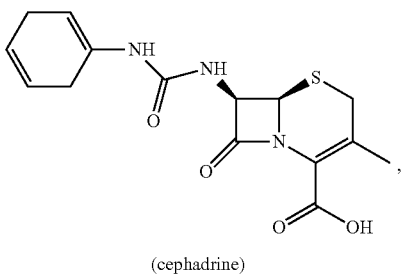
(cephadrine)

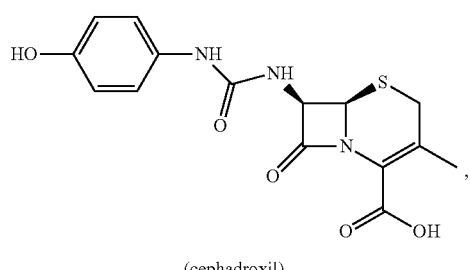
(cephadroxil)

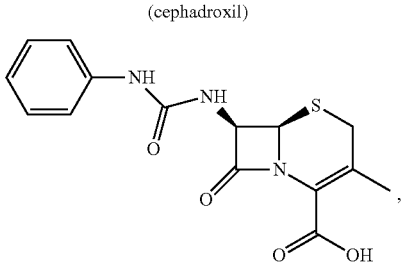
(cefalexin)

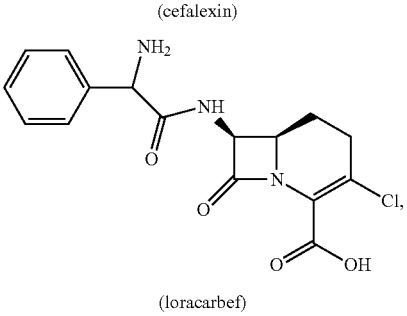
(loracarbef)

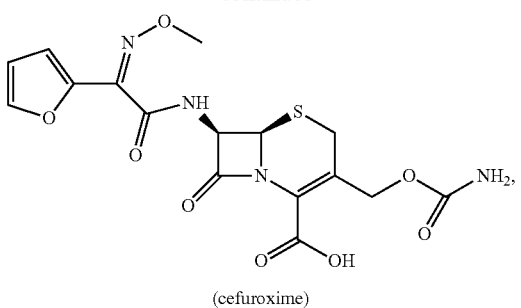
(cefuroxime)

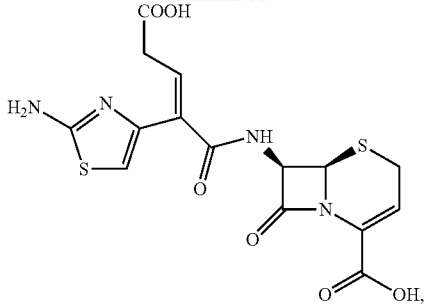
(ceftibuten)

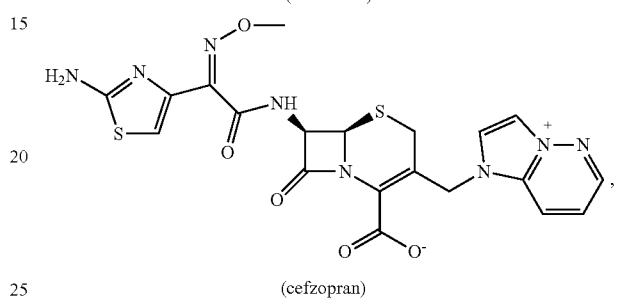
(cefzopran)

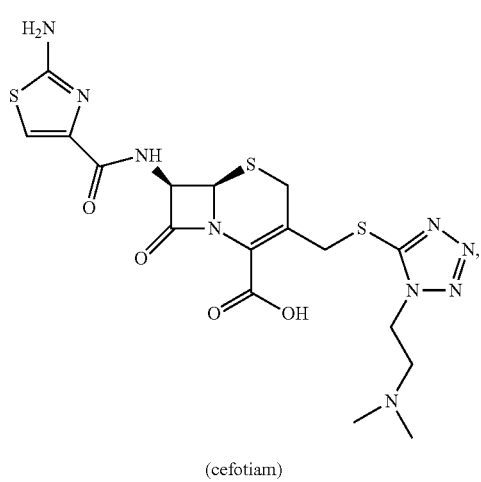
(cefotiam)

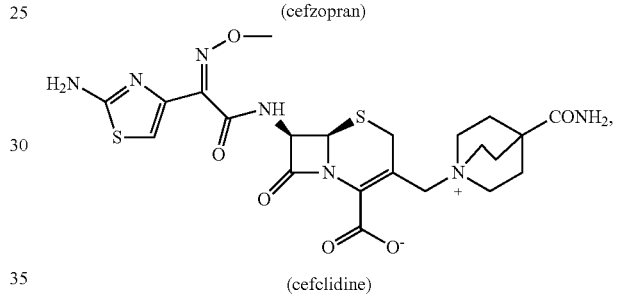
(cefclidine)

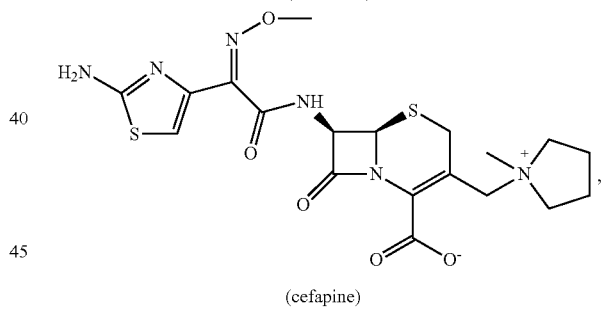
(cefapine)

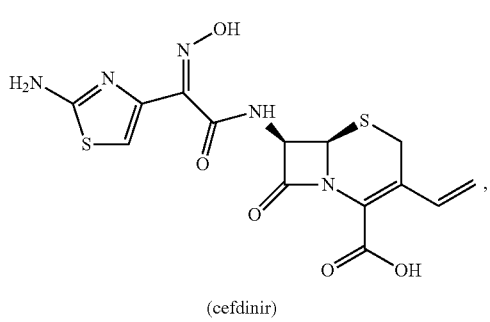
(cefdinir)

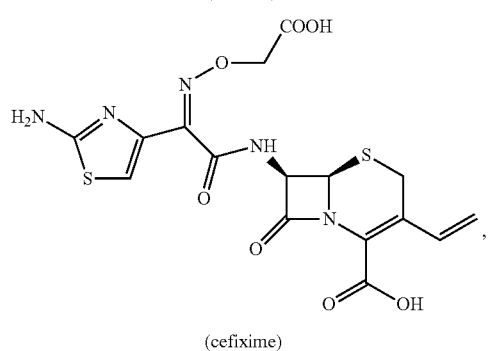
(cefixime)

deprotonated forms of any of the foregoing compounds, and combinations thereof. Cefzopran, cefclidine, and cefapine are examples of zwitterionic drugs.

Still other antibiotics include oxacephems (e.g., moxalactam and flomoxef), carbapenems (e.g., imipenenm, meropenem, ertapenem, doripena, panipenem, biapenem, razupenen, and tebipenem), monobactams (e.g., nocardicin A, aztreonam), and beta lactamase inhibitors (tazobactam and clavelanic acid), deprotonated forms of any of the foregoing compounds, and combinations thereof.

Exemplary NSAIDs include aspirin, mefenamic acid, meclofenamic acid, ibuprofen, diflunisal, flufenamic acid, tolfenamic acid, naproxen, salsalate, sulindac, diclofenac, fenoprofen, etodolac, oxaprozin, lumiracoxib, dexketoprofen, indometacin, ketorolac, loxoprofen, flurbiprofen, deprotonated forms of any of the foregoing compounds, and combinations thereof The bis-urea compounds are preferably prepared from a diamine of formula (6):

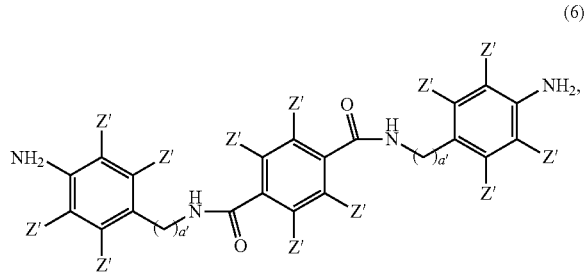

(6)

wherein
a' is 0 or 1, and
each Z' is an independent monovalent radical selected from the group consisting of hydrogen, halides, and functional groups comprising 1 to about 6 carbons.

In an embodiment, each Z' of formula (6) is hydrogen, and the diamine is a terephthalamide 4ABTA (a'=1 of formula (6)):

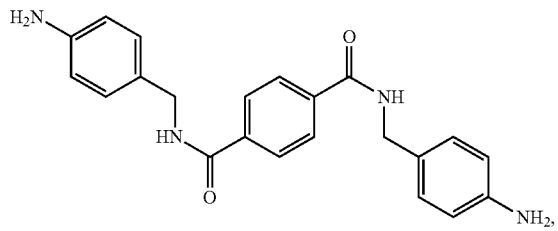

(4ABTA)

or terephthalamide 4APTA (a'=0 of formula (6)):

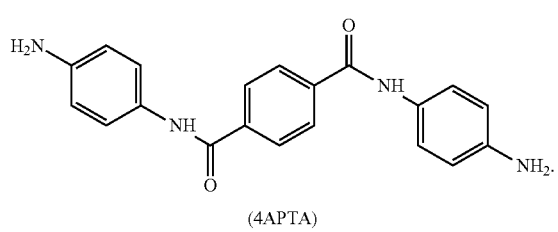 [SMILES: Nc1ccc(NC(=O)c2ccc(C(=O)Nc3ccc(N)cc3)cc2)cc1]

(4APTA)

Terephthalamide compounds 4ABTA and 4APTA can be prepared, for example, by reaction of recycled poly(ethylene terephthalate) (PET) using 4-aminobenzylamine and para-phenylenediamine, respectively, as demonstrated in the Examples further below.

Each of the amine groups of formula (6) can be coupled to another amine to form urea linkages using any suitable coupling agent (e.g., bis(pentafluorophenyl)carbonate (PFC)). The reaction with PFC forms an intermediate active pentafluorophenyl carbamate, which can then be treated with an amine-containing compound having a latent cationic, anionic, and/or zwitterionic group, thereby forming a precursor bis-urea compound comprising a latent cationic, anionic, and/or zwitterionic group, in a single pot reaction. The disclosed bis-urea compounds can then be prepared in one or more steps by subsequent deprotection and/or derivatization of the precursor bis-urea compound to generate the desired charged W' groups.

Also disclosed is a fiber comprising 3 or more self-assembled molecules of the disclosed bis-urea compounds, wherein i) the fiber has an average diameter of 4 nm to 10 nm, ii) the fiber has an aspect ratio of 100:1 or more, and iii) the self-assembled molecules are bound by non-covalent interactions in the fiber.

Further disclosed is a drug complex comprising a disclosed fiber and a drug, wherein i) the fiber and the drug are bound by non-covalent interactions and ii) the drug complex is suitable for controlled release of the drug.

Also disclosed are drug compositions comprising a solvent and a drug complex. The drug complex comprises a drug bound by non-covalent interactions to a fiber having the above-described features. In an embodiment, the drug is an antimicrobial drug. In another embodiment, the drug is an NSAID.

The drug composition can be effective in killing Gram-negative microbes, Gram-positive microbes, fungi, yeasts, and combinations thereof. In an embodiment, the bis-urea compound and the drug are present in the drug composition in a bis-urea compound:drug mole ratio of about 1:1. In another embodiment, the drug composition comprises about 0.02 wt % bis-urea compound and 0.009 wt % drug based on total weight of the drug composition.

EXAMPLES

Materials used in the following examples are listed in Table 1.

TABLE 1

| ABBREVI-ATION | DESCRIPTION | SUPPLIER |
|---|---|---|
| PET | Poly(ethylene terephthalate) flakes (1.92 g, 3 mm × 3 mm) obtained from recycled PET drink bottles | Arrowhead |
| TBD | 1,5,7-triazabicyclo[4.4.0]dec-5-ene | Sigma-Aldrich |
| TSB | Tryptic soy broth | BD Diagnostics (Singapore) |
| Bis-MPA | 2,2-Bis(methylol)propionic acid | Sigma-Aldrich |
| S. aureus | Staphylococcus aureus (ATCC No. 6538) | ATCC (U.S.A.) |
| PenG | Penicillin G potassium salt (MW 372.5) | Sigma Aldrich |

Tryptic soy broth (TSB) powder was purchased from BD Diagnostics (Singapore) and used to prepare the broth according to the manufacture's instruction. S. aureus (ATCC No. 6538) were obtained from ATCC (U.S.A) and re-cultured according to the suggested protocols. Penicillin G potassium salt (MW 372.5) was purchased from Sigma-Aldrich. All other chemicals were of analytical grade, and used as received.

Post-consumer water bottles purchased from Arrowhead were used as PET sources. The bottles were washed with water, dried in air at room temperature, and shredded by hand to a size of about 3 square millimeters to 5 square millimeters. The flakes were dried again in vacuum at 80° C. for at least 12 hours prior to the depolymerization reaction. The glass transition temperature of the post-consumer PET was 77° C., the melting point was 252° C.

Synthesis
Synthesis of MTC—OBn.

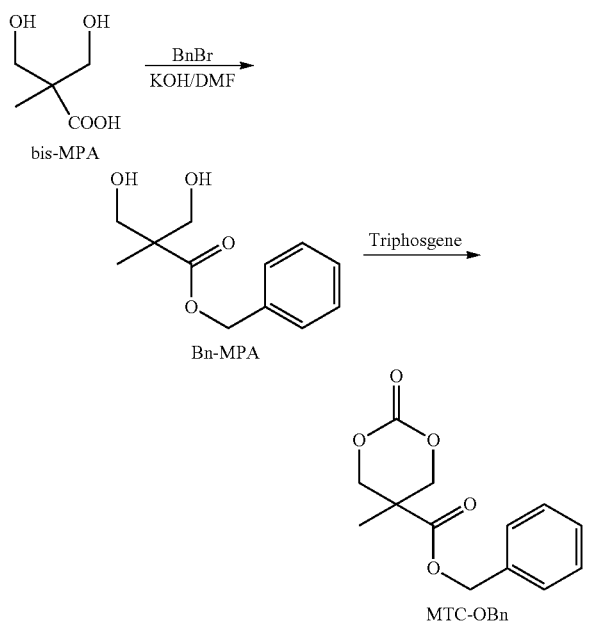

(i) A mixture of bis-MPA (45.0 g, 0.336 mol), potassium hydroxide (88% assay; 21.5 g, 0.338 mol), and DMF (250 mL) was heated to 100° C. for 1 hour at which point a homogenous solution was formed. Benzyl bromide (BnBr, 69.0 g, 0.404 mol) was added to the warm solution, and stirring was continued at 100° C. for 16 hours. The reaction was cooled and the solvent was removed under vacuum. Ethyl acetate (300 mL), hexanes (300 mL), and water (200 mL) were added to the residue. The organic layer was retained, washed with water (200 mL), dried (MgSO$_4$), and evaporated. The resulting solid was recrystallized from toluene (~1.2 ml/g crude) to give pure benzyl 2,2-bis(methylol)propionate (Bn-MPA, 46 g, 61%).

(ii) Benzyl 2,2-bis(methylol)propionate (Bn-MPA, 22.4 g, 0.100 mol) was dissolved in CH$_2$Cl$_2$ (300 mL) and pyridine (50 mL, 0.6 mol) and the solution was chilled to −78° C. under N$_2$. A solution of triphosgene (15.0 g, 50.0 mmol) in CH$_2$Cl$_2$ was added dropwise over 1 hour, at which point the reaction mixture was allowed to warm to room temperature for 2 hours. The reaction was quenched by addition of saturated aqueous NH$_4$Cl (150 mL), after which the organic layer was washed with 1 M aqueous HCl (3×200 mL), saturated aqueous NaHCO$_3$ (1×200 mL), dried (MgSO$_4$), filtered and evaporated to give 2a as a white solid (pinkish in some preparations) (24.3 g, 97%). Material for polymerization was purified by recrystallization from ethyl acetate.

Synthesis of MTCOH.

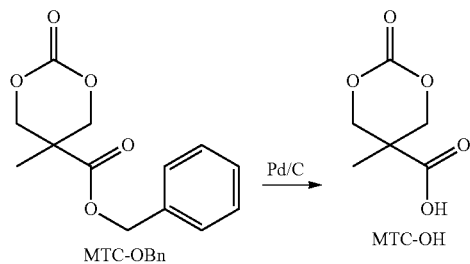 [SMILES: CC1(C(=O)OCc2ccccc2)COC(=O)OC1 ; CC1(C(=O)O)COC(=O)OC1]

A mixture of crude MTC—OBn (24.3 g, 97 mmol), ethyl acetate (250 mL), and Pd/C (10% w/w, 1.6 g) was swirled under H$_2$ (3 atm) for 24 hours. After evacuation of the H$_2$ atmosphere, THF (250 mL) was added and the mixture was filtered through THF-wetted Celite. Additional THF was used to ensure complete transfer. The collected washings were evaporated to give MTC—OH as a white solid that was used without further purification (15.6 g, 99+%).

Preparation of 5-methyl-5-(3-chloropropyl)oxycarboxyl-1,3-dioxan-2-one, (MTC-PrCl), MW 236.65

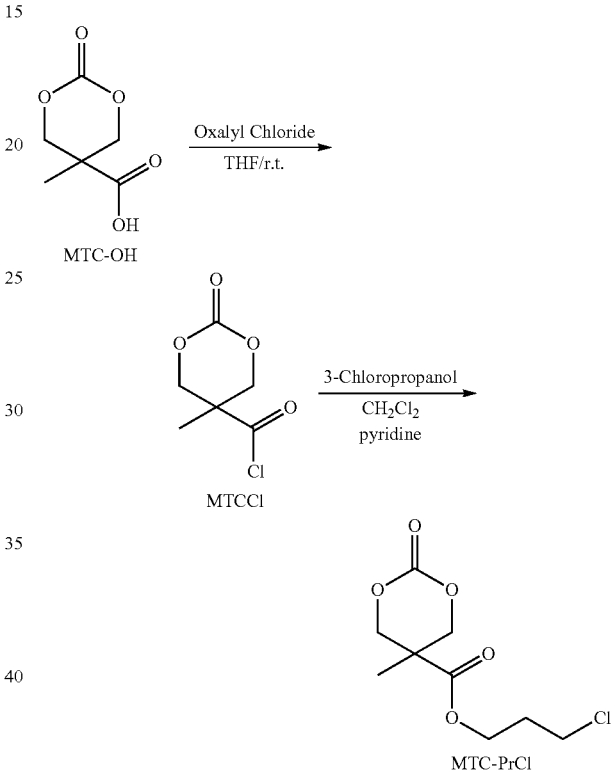

MTC—OH (8.82 g, 55 mmol) was converted to the acid chloride MTCCl using oxalyl chloride in THF at room temperature for 1 hour (99% yield). In a dry 250 mL round bottom flask equipped with a stir bar, the formed intermediate MTCCl was dissolved in 150 mL of dry methylene chloride. Under nitrogen flow an addition funnel was attached in which 3-chloropropanol (4.94 g, 4.36 mL, 52.25 mmol), pyridine (3.95 g, 4.04 mL, 55 mmol), and 50 mL of dry methylene chloride was charged. The flask was cooled to 0° C. using an ice bath and the top solution was added drop wise during a period of 30 minutes. The formed solution was stirred for an additional 30 minutes before the ice bath was removed and the solution was stirred for an additional 16 hours under nitrogen. The crude product MTC-PrCl was directly applied onto a silica gel column and the product was separated by eluting with 100% methylene chloride. The product fractions were removed and the solvent was evaporated, yielding the product as off-white oil, which crystallized upon standing. Yield 11 g (85%). $^1$H-NMR (CDCl$_3$) delta: 4.63 (d, 2H, CH$_2$), 4.32 (t, 2H, CH$_2$), 4.16 (d, 2H, CH$_2$), 3.55 (t, 2H, CH$_2$), 2.09 (m, 2H, CH$_2$), 1.25 (s, 3H, CH$_3$).

Example 1

Polyethylene Terephthalate (PET) Degradation with 4-Aminobenzylamine to Form 4ABTA

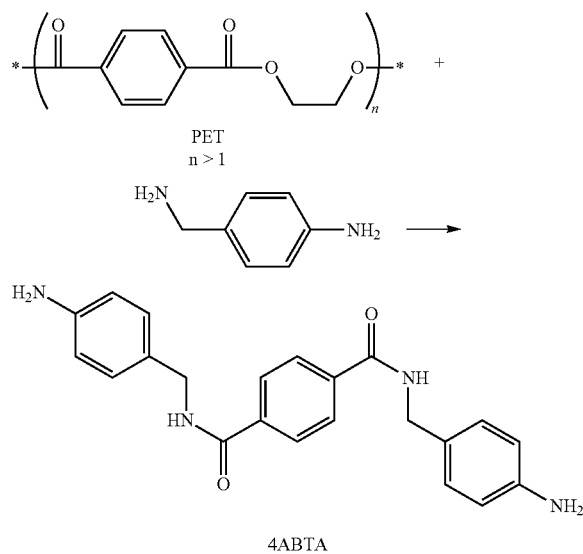

4ABTA

PET flakes (9.61 g, 0.05 mol), 4-aminobenzylamine (28.2 g, 0.23 mol) and 1,5,7-triazabicyclo[4.4.0]dec-5-ene (TBD, 0.36 g, 2.5 mmol) were placed in a 250 ml flask and then heated under nitrogen atmosphere at 120° C. for 3 hours, resulting in a solidified reaction mixture. The mixture was triturated and washed in isopropanol (200 ml). The residue was rinsed with THF and diethylether several times, then dried in a vacuum oven at 80° C., yielding a white powder as a product, bis(4-aminobenzyl)terephthalamide (4ABTA: 15.15 g, 81%). $^1$H-NMR (400 MHz, DMSO-$d_6$): delta 8.96 (t, J=6 Hz, 2H, NH), 7.93 (s, 4H, Ar—H), 6.98 (d, J=8 Hz, 4H, Ar—H), 6.51 (d, J=8 Hz, Ar—H), 4.96 (s, 4H, NH$_2$), 4.30 (d, J=6 Hz, 4H, CH$_2$). $^{13}$C-NMR (100 MHz, DMSO-$d_6$): δ 165.4, 147.6, 136.7, 128.4, 127.3, 126.4, 113.8, 42.5. m.p. (DSC): 203° C.

Example 2

PET Degradation with p-Phenylenediamine to Form 4APTA

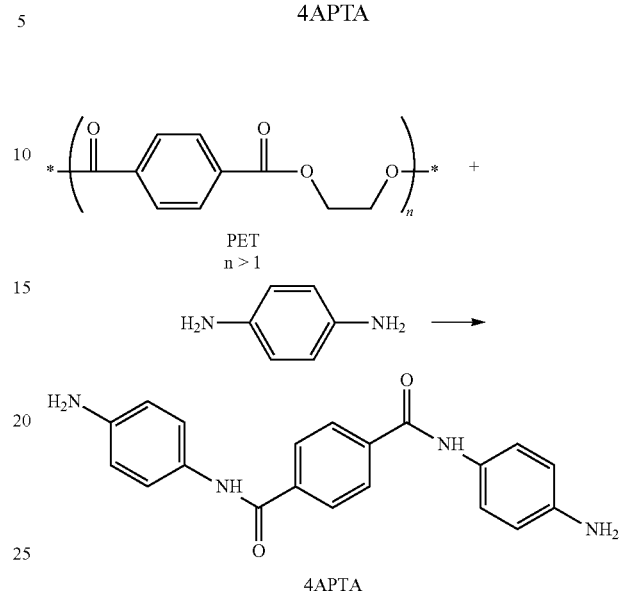

4APTA

PET flakes (0.48 g, 2.5 mmol), p-phenylenediamine (4.09 g, 38 mmol) and TBD (17.7 mg, 0.127 mmol) were placed in a 25 ml Schlenk tube and then heated under nitrogen atmosphere at 190° C. for 18 hours. The homogeneous solution was then poured in 100 ml of THF and filtered. The residue was then washed in hot water (50 ml) and dried in a vacuum oven at 80° C., yielding a gray powder as a product, bis(4-aminophenyl)terephthalamide (4APTA: 0.63 g, 72%). $^1$H-NMR (400 MHz, DMSO-$d_6$): δ 10.0 (s, 2H, NH), 8.02 (s, 4H, Ar—H), 7.39 (d, J=8.8 Hz, 4H, Ar—H), 6.55 (d, J=8.8 HZ, 4H, Ar—H), 4.97 (s, 4H, NH$_2$). $^{13}$C-NMR (100 MHz, DMSO-$d_6$): δ 163.8, 145.3, 137.3, 127.8, 127.3, 122.2, 113.6. mp (DSC): 301° C.

Example 3

Preparation of Cationic Compound C-2

1) Preparation of C-1, by coupling of 3-(dimethylamino)-1-propylamine to ABTA:

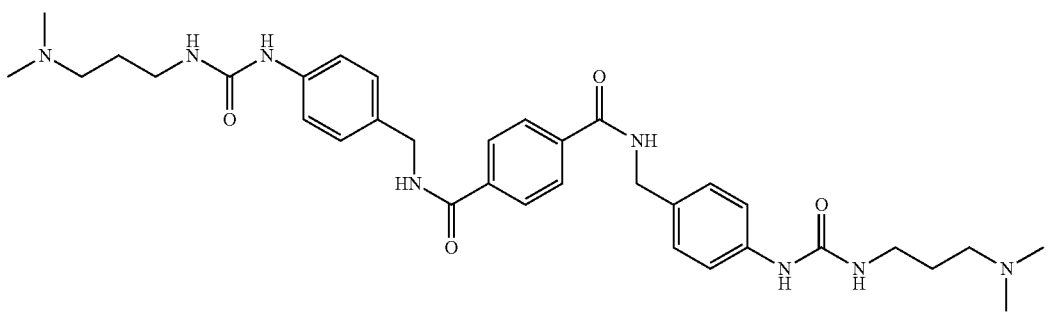

C-1

To a dry DMF solution (8 mL) of bis(pentafluorophenyl) carbonate (PFC, 2.02 g, 5.13 mmol) was added a solution of 4ABTA (0.75 g, 2.0 mmol) in dry DMF (5 mL). The reaction mixture was stirred for 1 hour at room temperature. Subsequently, 3-(dimethylamino)-1-propylamine (0.71 g, 6.96 mmol) was added, and the mixture was kept stirring for 2 hours. To remove excess PFC and the amine reagent, the product was precipitated in diethylether (200 mL). Thereafter, the product was filtered and dried in vacuum (60° C.) to yield C-1 (1.10 g, 86%). $^1$H-NMR (400 MHz, DMSO-$d_6$): delta 9.09 (t, J=5.4 Hz, 2H, Ar—CONH), 8.49 (s, 2H, Ar—NH), 7.95 (s, 4H, Ar—H), 7.33 (d, J=8.4 Hz, 4H, Ar—H), 7.17 (d, J=8.4 Hz, 4H, Ar—H), 6.19 (t, J=5.6 Hz, 2H, NHCH$_2$), 4.39 (d, J=5.6 Hz, 2H, Ar—CH$_2$), 3.08 (ddd, J=6.4, 6.4, 6.4 Hz, 4H, CH$_2$NH), 2.33 (t, J=7.2 Hz, 4H, NCH$_2$), 2.21 (s, 12H, CH$_3$), 1.57 (quin, J=7.0 Hz, 4H, CH$_2$). $^{13}$C-NMR (100 MHz, DMSO-$d_6$): delta 165.3, 155.2, 139.3, 136.6, 131.8, 127.7, 127.2, 117.5, 56.3, 44.6, 42.2, 37.2, 27.2.

2) Quaternization of C-1 with iodomethane to form C-2:

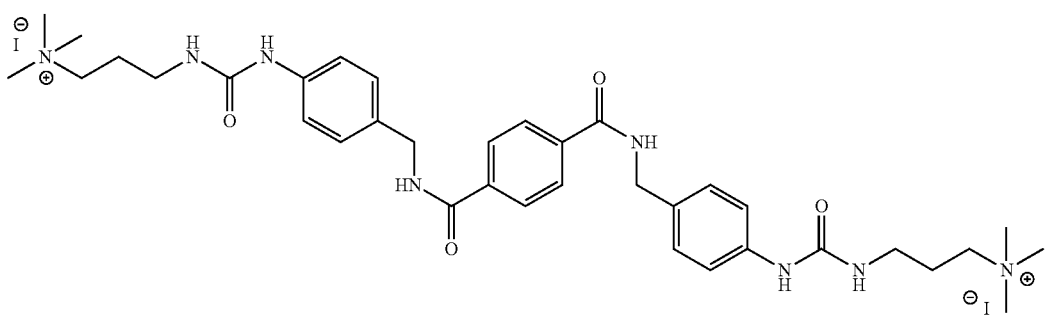

C-2

To a dry DMF solution (15 ml) of C-1 (0.95 g, 1.50 mmol) was added iodomethane (300 microliters, 4.8 mmol). As the iodomethane was added, the cloudy C-1 solution became clear. The reaction mixture was stirred for 1 hour at room temperature and precipitated in diethylether (150 ml). The precipitate was filtered and washed with diethylether a few times and dried in vacuum (60° C.) to yield C-2 (0.85 g, 62%, MW 914.66, Chemical Formula: C36H52I2N8O4) $^1$H-NMR (400 MHz, DMSO-$d_6$): delta 9.09 (t, J=5.8 Hz, 2H, Ar—CONH), 8.52 (s, 2H, Ar—NH), 7.95 (s, 4H, Ar—H), 7.34 (d, J=8.4 Hz, 4H, Ar—H), 7.18 (d, J=8.4 Hz, 4H, Ar—H), 6.23 (t, J=5.8 Hz, 2H, NHCH$_2$), 4.39 (d, J=6.0 Hz, 2H, Ar—CH$_2$), 3.33-3.26 (m, 4H, CH$_2$N), 3.14 (ddd, J=6.4, 6.4, 6.4 Hz, 4H, CH$_2$NH), 3.05 (s, 18H, CH$_3$), 1.90-1.80 (m, 4H, CH$_2$)

Example 4

Preparation of C-4

1) Coupling of tert-butyl(4-aminobutyl)carbamate to 4ABTA to form:

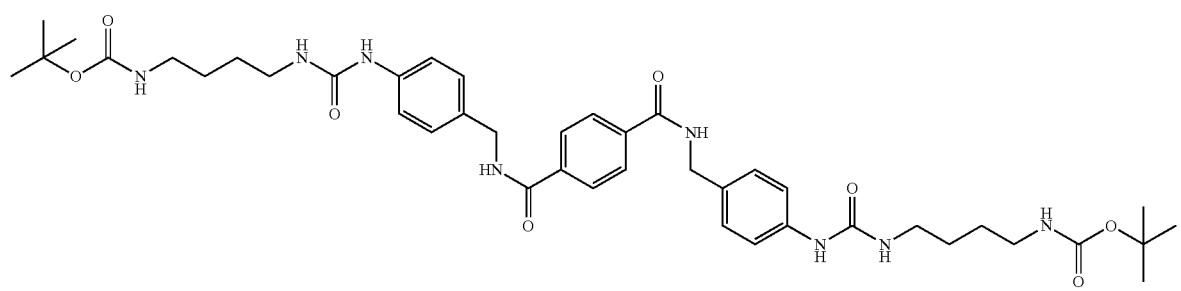

C-3

To a dry DMF solution (16 mL) of PFC (3.97 g, 10.1 mmol) was added a solution of 4ABTA (1.50 g, 4.0 mmol) in dry DMF (8 mL). The reaction mixture was stirred for 1 hour at room temperature. Subsequently, tert-butyl(4-aminobutyl) carbamate (2.36 g, 12.6 mmol) was added, and the mixture was kept stirring overnight. To remove excess PFC and the amine reagent, the reaction mixture was precipitated in diethylether (250 mL). Thereafter, the product was filtered and dried in vacuum (60° C.) to yield C-3 (2.87 g, 90%, MW 802.96, Chemical Formula: C42H58N8O8). $^1$H-NMR (400 MHz, DMSO-d$_6$): delta 9.08 (t, J=5.8 Hz, 2H, Ar—CONH), 8.36 (s, 2H, Ar—NH), 7.95 (s, 4H, Ar—H), 7.32 (d, J=8.4 Hz, 4H, Ar—H), 7.17 (d, J=8.4 Hz, 4H, Ar—H), 6.82 (t, J=5.6 Hz, 2H, NHCOO), 6.07 (t, J=5.6 Hz, 2H, NHCH$_2$), 4.39 (d, J=5.6 Hz, 2H, Ar—CH$_2$), 3.09-3.00 (m, 4H, CH$_2$NHCOO), 2.95-2.86 (m, 4H, NHCH$_2$), 1.41-1.32 (m, 26H, CH$_2$ and CH$_3$). $^{13}$C-NMR (100 MHz, DMSO-d$_6$): δ 165.3, 155.5, 155.1, 139.3, 136.6, 131.8, 127.7, 127.2, 117.4, 77.3, 42.2, 39.6, 38.7, 28.2, 27.2, 27.0.

2) Deprotection of C-3 to form C-4:

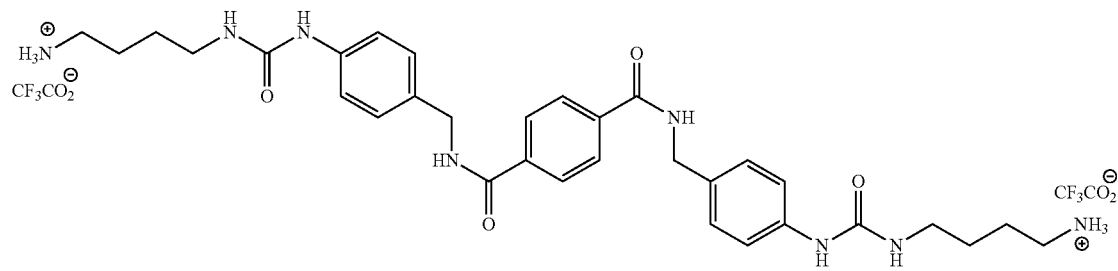

C-4

C-3 (2.50 g, 3.11 mmol) was added into trifluoroacetic acid (10 ml, 130.6 mol) and the mixture was stirred overnight. As the deprotection proceeds, the reaction mixture became homogeneous. The reaction mixture was then precipitated in diethylether (200 ml) and the precipitate was filtered and washed with diethylether a few times and dried in vacuum (60° C.) to yield C-4 (2.07 g, 80%, MW 830.77, Chemical Formula: C36H44F6N8O8). $^1$H-NMR (400 MHz, DMSO-d$_6$): delta 9.09 (t, J=5.8 Hz, 2H, Ar—CONH), 8.56 (s, 2H, Ar—NH), 7.95 (s, 4H, Ar—H), 7.72 (b, 6H, NH$_3^+$), 7.34 (d, J=8.4 Hz, 4H, Ar—H), 7.17 (d, J=8.4 Hz, 4H, Ar—H), 6.30 (t, J=5.8 Hz, 2H, NHCH$_2$), 4.39 (d, J=5.6 Hz, 2H, Ar—CH$_2$), 3.08 (ddd, J=6.2, 6.2, 6.0 Hz, 4H, CH$_2$NH), 2.80 (t, J=7.4 Hz, 4H, CH$_3$), 1.59-1.39 (m, 8H, CH$_2$). $^{13}$C-NMR (100 MHz, DMSO-d$_6$): 165.3, 158.4, 155.3, 139.4, 136.6, 131.8, 127.7, 127.2, 117.5, 74.7 (t), 42.2, 38.6, 38.3, 26.8, 24.4.

Example 5

Preparation of C-6

1) Coupling of 3-(dimethylamino)-1-propylamine to 4APTA to form C-5 KF512:

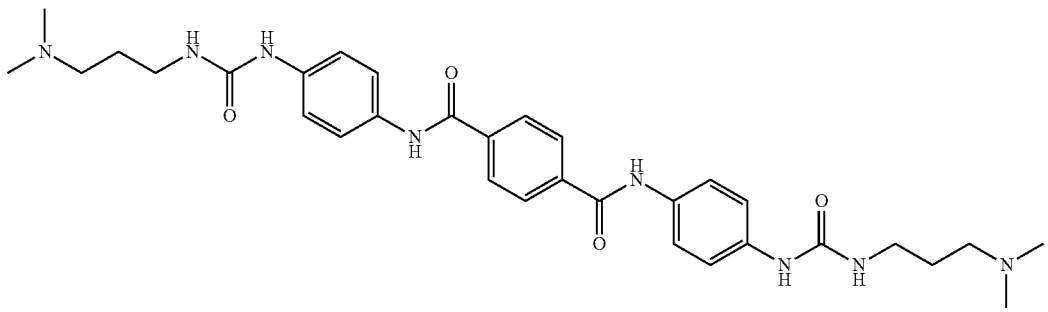

C-5

To a dry DMF solution (4 mL) of PFC (1.0 g, 2.53 mmol) was added a solution of 4APTA (0.35 g, 1.0 mmol) in dry DMF (4 mL). The reaction mixture was stirred for 1 hour at room temperature. Subsequently, 3-(dimethylamino)-1-propylamine (0.38 g, 3.68 mmol) was added, and the mixture was kept stirring overnight. To remove excess PFC and the amine reagent, the reaction mixture was precipitated in diethylether (100 mL). Thereafter, the product was filtered and dried in vacuum (60° C.) to yield C-5 (0.51 g, 84%, MW 602.73, Chemical Formula: C32H42N8O4). $^1$H-NMR (400 MHz, DMSO-$d_6$): delta 10.3 (s, 2H, Ar—CONH), 8.52 (s, 2H, Ar—NH), 8.06 (s, 4H, Ar—H), 7.63 (d, J=9.2 Hz, 4H, Ar—H), 7.37 (d, J=8.8 Hz, 4H, Ar—H), 6.23 (t, J=5.6 Hz, 2H, NHCH$_2$), 3.12 (ddd, J=6.4, 6.4, 6.0 Hz, 4H, CH$_2$NH), 2.57 (t, J=7.2 Hz, 4H, NCH$_2$), 2.40 (s, 12H, CH$_3$), 1.66 (quin, J=7.0 Hz, 4H, CH$_2$). $^{13}$C-NMR (100 MHz, DMSO-$d_6$): δ 164.3, 155.4, 137.3, 136.6, 132.4, 127.5, 121.1, 117.8, 55.6, 43.6, 36.8, 26.4.

2) Quaternization of C-5 with iodomethane to form C-6:

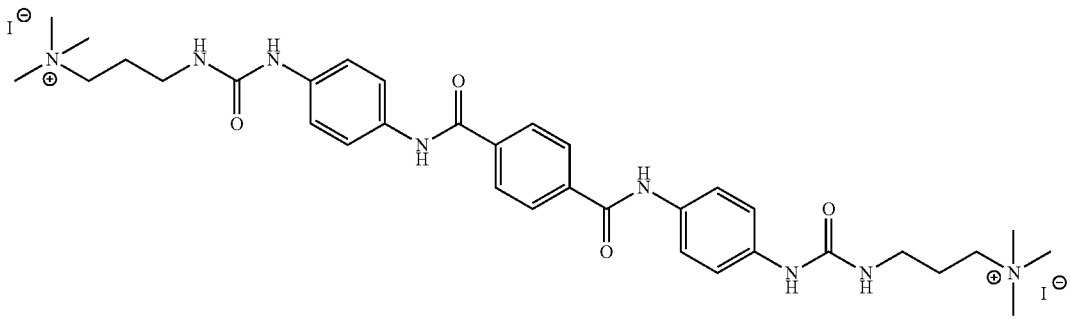

C-6

To a dry DMF solution (10 ml) of C-5 (0.91 g, 1.50 mmol) was added iodomethane (300 microliters, 4.8 mmol). As iodomethane was added, the cloudiness of the reaction mixture became light. The reaction mixture was stirred overnight at room temperature and precipitated in diethylether (150 ml). The precipitate was filtered and washed with THF a few times and dried in vacuum (60° C.) to yield C-6 (0.69 g, 52%, MW 886.61, Chemical Formula: C34H48I2N8O4). $^1$H-NMR (400 MHz, DMSO-$d_6$): delta 10.3 (s, 2H, Ar—CONH), 8.55 (s, 2H, Ar—NH), 8.06 (s, 4H, Ar—H), 7.64 (d, J=8.4 Hz, 4H, Ar—H), 7.39 (d, J=8.8 Hz, 4H, Ar—H), 6.25 (t, J=5.8 Hz, 2H, NHCH$_2$), 3.37-3.27 (m, 4H, CH$_2$N), 3.16 (ddd, J=6.0, 6.0, 5.6 Hz, 4H, CH$_2$NH), 3.06 (s, 18H, CH$_3$), 1.93-1.82 (m, 4H, CH$_2$). $^{13}$C-NMR (100 MHz, DMSO-$d_6$): δ 164.3, 155.3, 137.3, 136.5, 132.5, 127.5, 121.1, 117.9, 63.5, 52.2, 36.3, 23.7.

Example 6

Preparation of Cationic Compound C-8

1) Coupling of 5-amino-1-pentanol to 4ABTA to produce HPUBT.

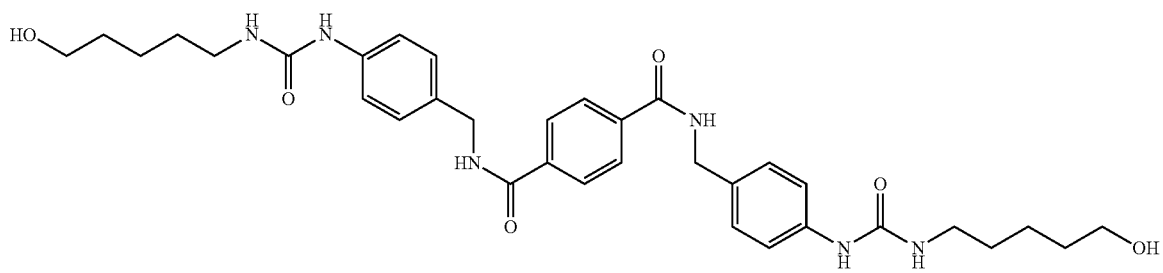

HPUBT

To a dry DMF solution (20 mL) of PFC (9.07 g, 23.0 mmol) was added a solution of 4ABTA (3.75 g, 10.0 mmol) in dry DMF (30 mL). The reaction mixture was stirred for 1 hour at room temperature. Subsequently, a DMF solution (5 mL) of 5-amino-1-pentanol (3.98 g, 38.6 mmol) was added, and the mixture was kept stirring overnight. To remove excess PFC and the amine reagent, the reaction mixture was precipitated in methanol (400 mL) and rinsed with methylene chloride a few times. Thereafter, the product was filtered and dried in vacuum (60° C.) to yield bis(4-(3-(5-hydroxypentyl)ureido) benzyl)terephthalamide (HPUBT: 5.50 g, 87%, MW 632.75, Chemical Formula: C34H44N6O6). $^1$H-NMR (400 MHz, DMSO-d$_6$): delta 9.09 (t, J=6.0 Hz, 2H, Ar—CONH), 8.37 (s, 2H, Ar—NH), 7.95 (s, 4H, Ar—H), 7.32 (d, J=8.4 Hz, 4H, Ar—H), 7.17 (d, J=8.8 Hz, 4H, Ar—H), 6.08 (t, J=5.8 Hz, 2H, NHCH$_2$), 4.43-4.34 (m, 6H, OH and Ar—CH$_2$), 3.38 (ddd, J=5.8, 5.8, 6.4 Hz, 4H, CH$_2$OH), 3.05 (ddd, J=6.2, 6.2, 6.4 Hz, 4H, NHCH$_2$), 1.47-1.35 (m, 8H, CH$_2$), 1.34-1.23 (m, 4H, CH$_2$). $^{13}$C NMR (125 MHz, DMSO-d$_6$): delta 165.4, 155.1, 139.3, 136.6, 131.8, 127.7, 127.2, 117.4, 60.6, 42.3, 32.2, 29.6, 22.9. (One signal was not detectable, presumably due to overlapping with DMSO signals)

2) Ring-opening of MTC-PrCl with HPUBT to produce C-7:

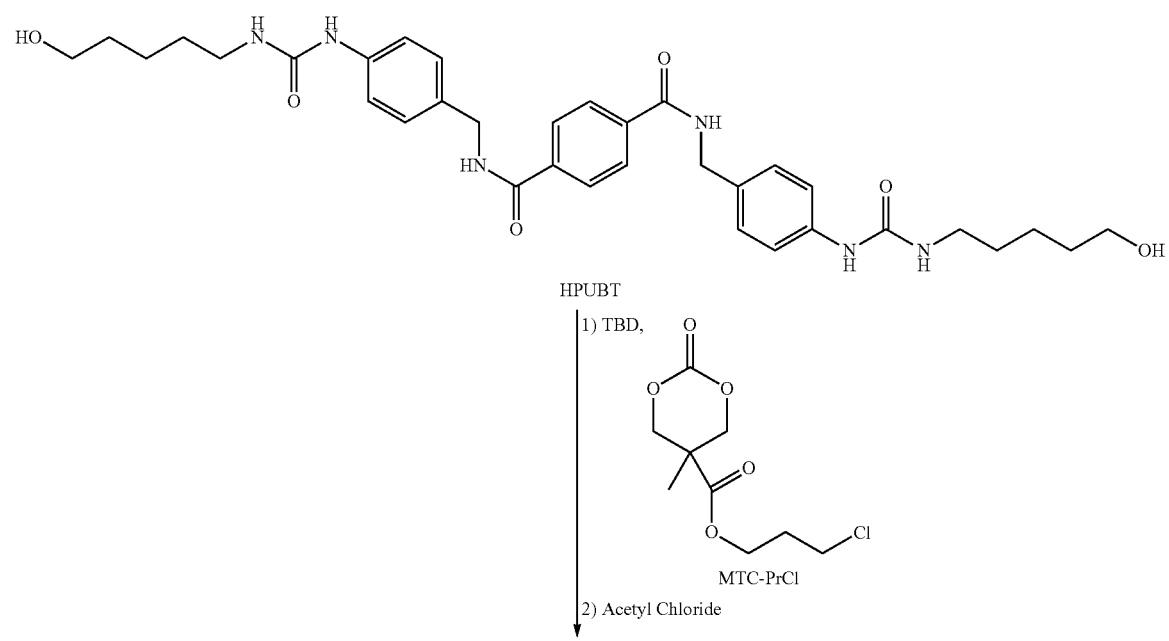

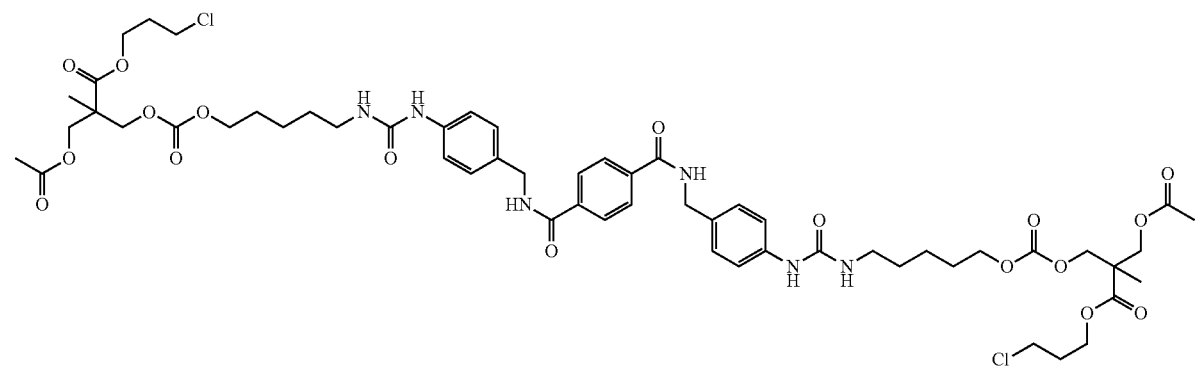

C-7

In a nitrogen glove box, HPUBT (0.63 g, 1.0 mmol) was dissolved in dry DMSO (6 mL) upon heating. After the solution became homogeneous, MTC-PrCl (0.72 g, 3.0 mmol) was directly added to the solution followed by TBD (14.5 mg, 0.10 mmol). The reaction mixture was stirred overnight without heating and precipitated in isopropanol (150 ml). The residue was then dissolved in a mixed solvent (5 ml) of dry THF and DMF (3:2) and subjected to acylation by addition of triethylamine (0.21 g, 2.1 mmol) and acetyl chloride (0.18 g, 2.3 mmol). The reaction was stirred overnight, precipitated in isopropanol, rinsed with diethylether, and dried in vacuum (60° C.) to yield C-7 (0.57 g, 48%, MW 1190.12, Chemical Formula: C56H74C12N6O18). $^1$H-NMR (400 MHz, DMSO-$d_6$): delta 9.07 (t, J=6.0 Hz, 2H, Ar—CONH), 8.36 (s, 2H, Ar—NH), 7.95 (s, 4H, Ar—H), 7.32 (d, J=8.4 Hz, 4H, Ar—H), 7.17 (d, J=8.4 Hz, 4H, Ar—H), 6.09 (t, J=5.6 Hz, 2H, NHCH$_2$), 4.39 (d, J=5.2 Hz, 2H, Ar—CH$_2$), 4.29-4.00 (m, 16H, CH$_2$OCOO, CCH$_2$O, CH$_2$CH$_2$OCO), 3.70-3.61 (m, 4H, CH$_2$Cl), 3.05 (ddd, J=6.2, 6.2, 6.0 Hz, 4H, CH$_2$NH), 2.06-1.93 (m, 10H, CH$_2$CH$_2$Cl, COCH$_3$), 1.66-1.54 (m, 4H, CH$_2$CH$_2$O), 1.47-1.37 (m, 4H, CH$_2$CH$_2$NH), 1.35-1.25 (m, 4H, CH$_2$), 1.17 (s, 6H, CH$_3$).

3) Quaternization of C-7 with trimethylamine to form C-8:

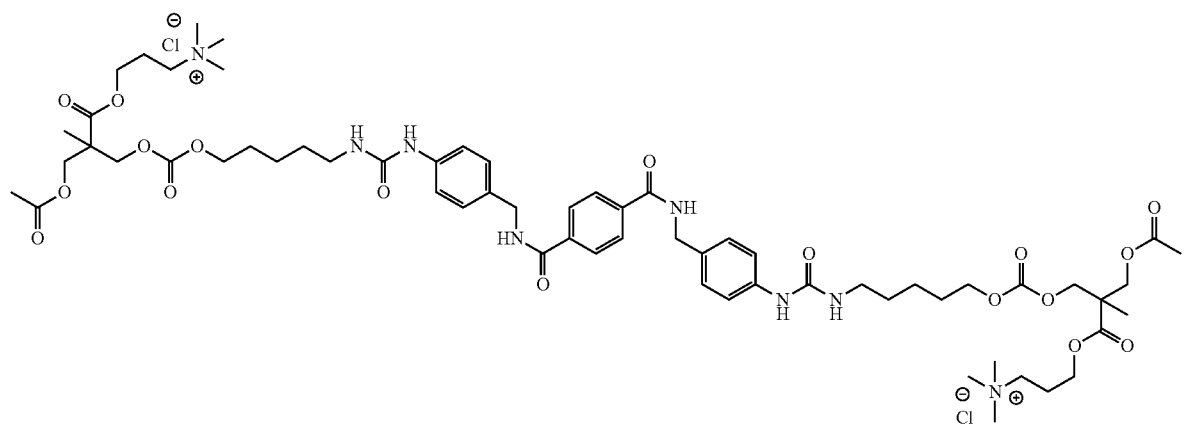

C-8

Trimethylamine gas (2.31 g, 39 mmol) was charged to a DMF solution (10 mL) of C-7 (0.57 g, 0.47 mmol) immersed in a dry-ice/acetone bath. The solution was then allowed to warm to room temperature over 2 hours and then kept stirring overnight at 50° C. Excess of trimethylamine was removed upon subsequently purging the solution with nitrogen gas for 1 hour and evaporating in vacuum. The residue was precipitated in diethylether, isolated and dried in vacuum to give C-8 (0.50 g, 81%, MW 1308.34, Chemical Formula: C62H92Cl2N8O18).

Example 7
Synthesis of Cationic Compound C-10
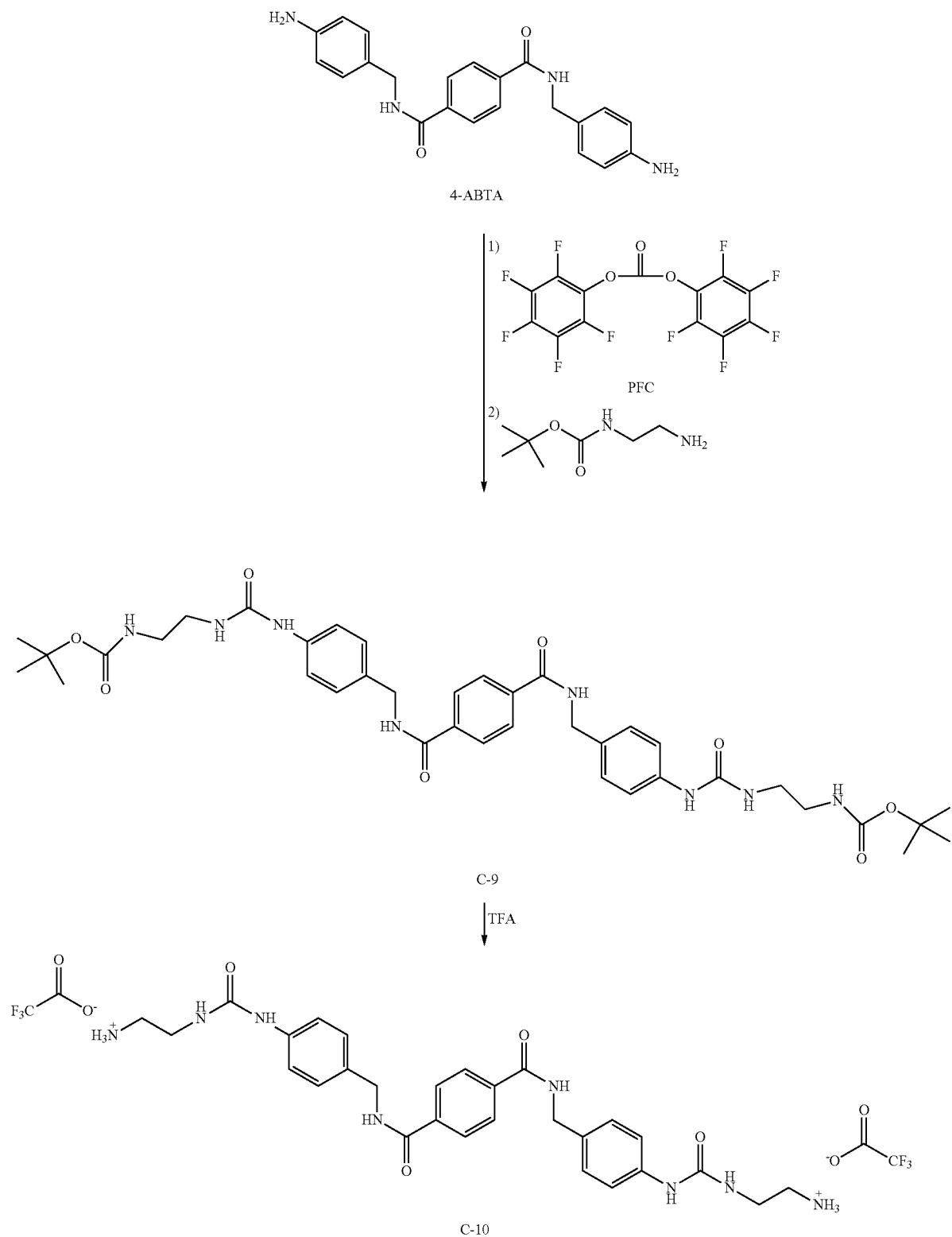

In a small vial, $N^1,N^4$-bis(4-aminobenzyl)terephthalamide (4ABTA) (748.9 mg, 2.0 mmol) was dissolved in DMF (4 mL). This solution was slowly added to a solution of PFC (1.97 g, 5 mmol) dissolved in DMF (8 mL) and the resulting solution was stirred for 1.5 hours. To this solution, tert-butyl (2-aminoethyl)carbamate (0.96 g, 6 mmol) was added and the reaction mixture was stirred overnight. The compound C-9 was precipitated into ether and isolated as an off-white powder by filtration. The compound was dissolved in 4 mL of trifluoroacetic acid (TFA) and stirred overnight at 50° C. to ensure deprotection, forming C-10 (MW 774.67, Chemical Formula: C32H36F6N8O8). $^1$H-NMR (400 MHz, DMSO-$d_6$): delta 10.3 (s, 2H,), 8.82 (s, 2H, 9), 8.06 (s, 4H,), 7.72 (d, J=8.8 Hz, 4H,), 7.37 (d, J=8.8 Hz, 4H,), 6.10 (t, J=5.8 Hz, 2H,),), 4.43-4.34 (m, 4H), 3.37-3.39 (m, 4H), 2.73-2.9 (m, 4H).

Example 8

Synthesis of Cationic Compound C-12

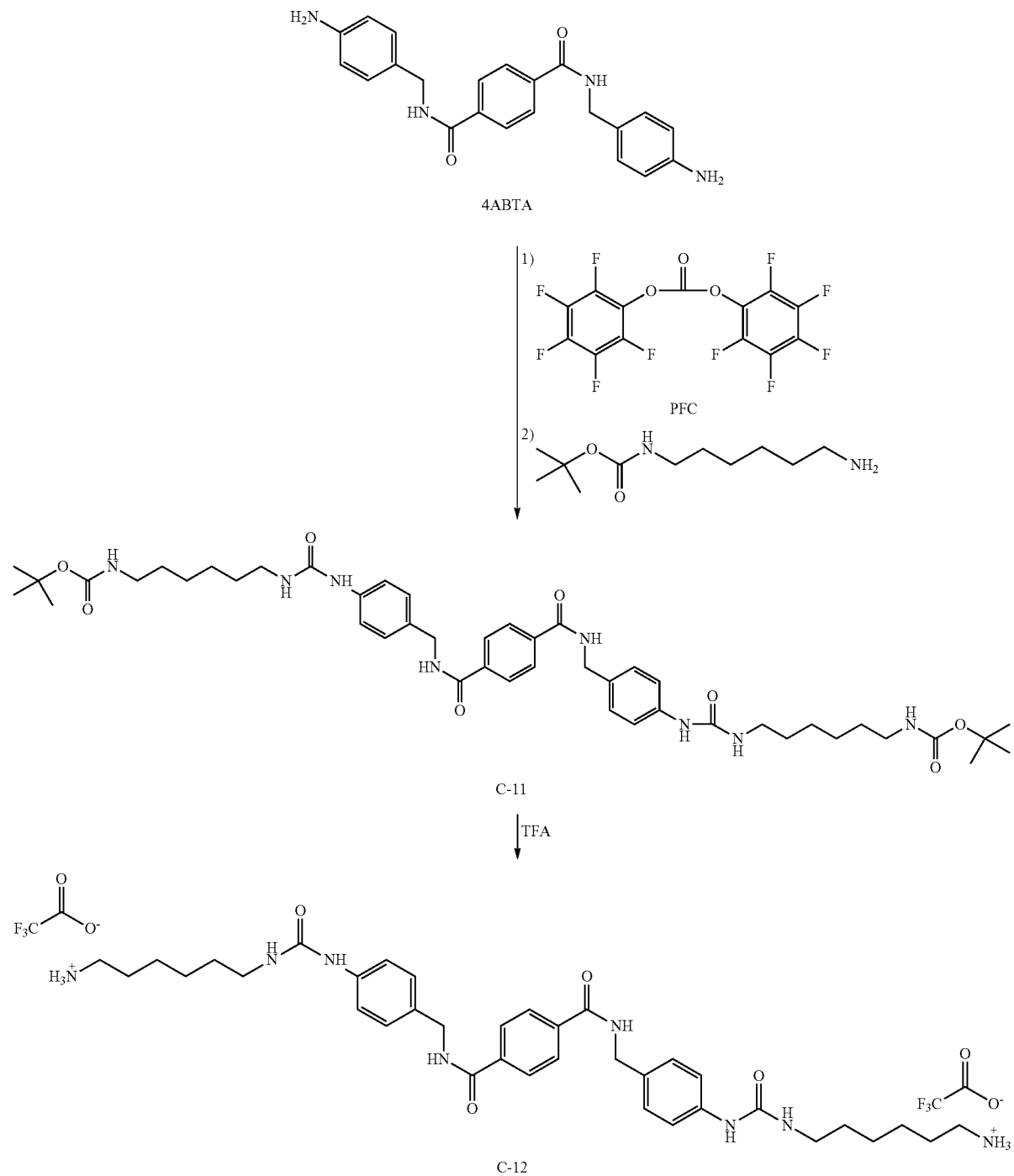

In a small vial, $N^1,N^4$-bis(4-aminobenzyl)terephthalamide (4ABTA) (700.0 mg, 1.87 mmol) was dissolved in DMF (4 mL). This solution was slowly added to a solution of PFC (1.97 g, 5 mmol) dissolved in DMF (8 mL) and the resulting solution was stirred for 1.5 hours. To this solution, tert-butyl (6-aminohexyl)carbamate (1.20 g, 6 mmol) was added and the reaction mixture was stirred overnight. The compound C-11 was precipitated into ether and isolated as an off-white powder by filtration. The compound was dissolved in 4 mL of TFA and allowed to react overnight at 50° C. to ensure deprotection forming C-12 (MW 886.88 Chemical Formula: $C40H52F6N8O8$). $^1$H-NMR (400 MHz, DMSO-$d_6$): delta 10.3 (s, 2H,), 8.82 (s, 2H, 9), 8.06 (s, 4H,), 7.72 (d, J=8.8 Hz, 4H,), 7.37 (d, J=8.8 Hz, 4H,), 6.10 (t, J=5.8 Hz, 2H,), 4.43-4.34 (m, 4H), 3.3-3.45 (m, 4H), 2.85-2.95 (m, 4H), 1.50-1.60 (m, 4H), 1.35-1.44 (m, 4H), 1.20-1.33 (m, 4H).

Example 9

Synthesis of Cationic Compound C-14

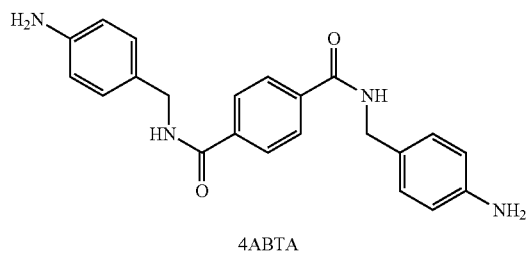

4ABTA

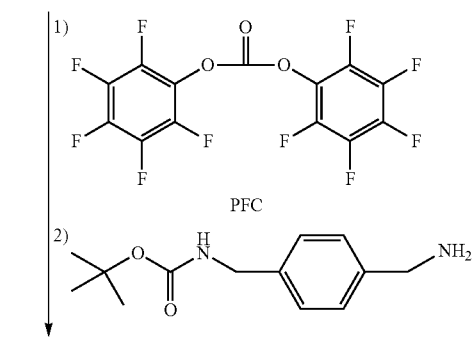

PFC

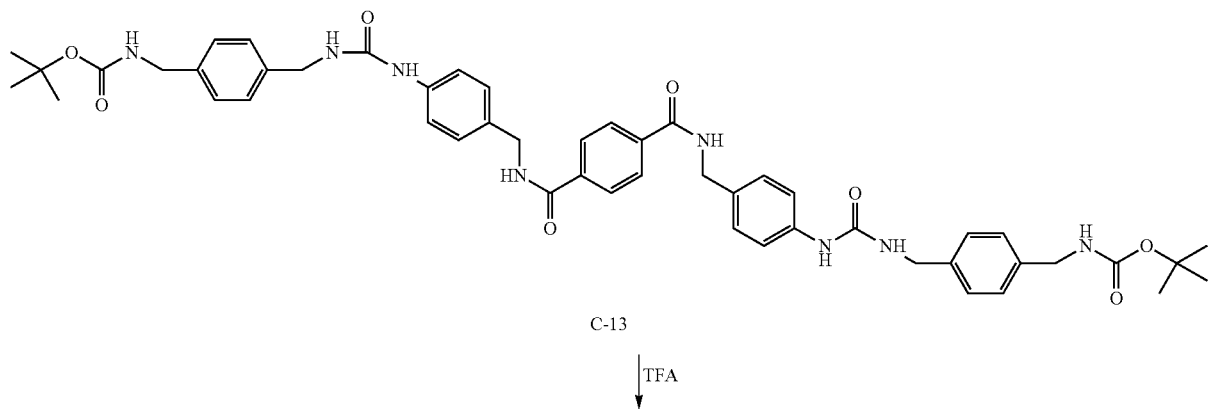

C-13

TFA

-continued

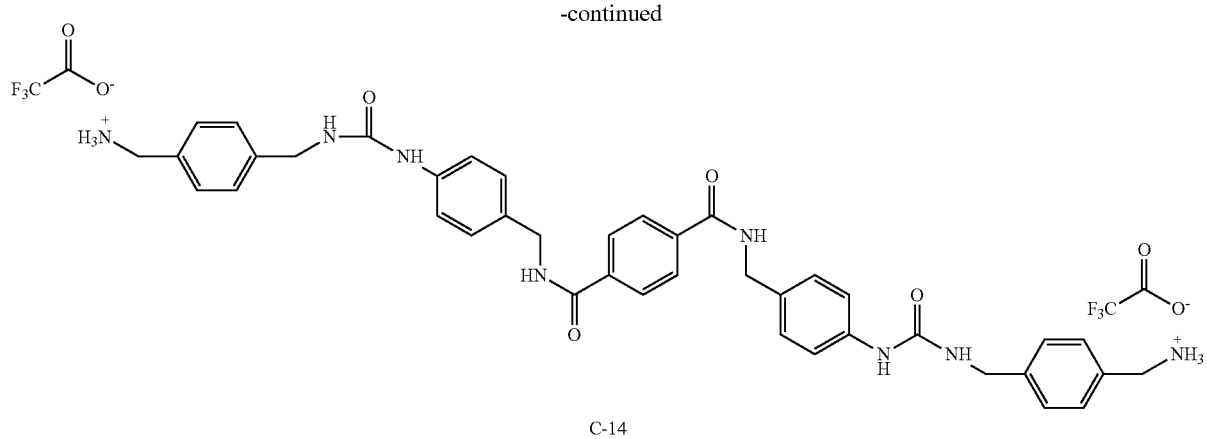

C-14

In a small vial, $N^1,N^4$-bis(4-aminobenzyl)terephthalamide (4ABTA) (600.0 mg, 1.60 mmol) was dissolved in DMF (4 mL). This solution was slowly added to a solution of PFC (1.97 g, 5 mmol) dissolved in DMF (8 mL) and the resulting solution was stirred for 1.5 hours. To this solution, tert-butyl 4-(aminomethyl)benzylcarbamate (1.13 g, 6 mmol) was added and the reaction mixture was stirred overnight. The compound C-13 was dissolved in 4 mL of TFA and allowed to react overnight at 50° C. to ensure deprotection forming C-14 (MW 926.86, Chemical Formula: C44H44F6N8O8). $^1$H-NMR (400 MHz, DMSO-$d_6$): delta 9.1 (s, 2H,), 8.87 (s, 2H), 8.06 (s, 4H,), 7.9-8.0 (d, J=8.8 Hz, 4H,), 2.21 (m, 4H), 7.15 (d, J=8.8 Hz, 4H,), 6.10 (t, J=5.8 Hz, 2H,),), 4.43-4.34 (m, 4H), 2.2-4.35 (m, 4H), 3.9-4.1 (m, 4H).

Table 2 summarizes the above-prepared cationic compounds, their critical micelle concentrations, and the zeta potentials of the self-assembled fibers formed. The zeta potential of the self-assembled cationic compounds in de-ionized (DI) water was measured by Zetasizer 3000 HAS (Malvern Instrument Ltd., Malvern, UK) equipped with a He—Ne laser beam at 658 nm (scattering angle: 90°). The concentration of cationic compounds was 1000 mg/L. Each measurement was repeated 5 times. An average value was obtained from the five measurements.

TABLE 2

| Example | Name | Molecular weight | CMC (mg/L) | Zeta Potential (mV) |
|---|---|---|---|---|
| 3 | C-2 | 914.66 | 170.0 | 47.0 |
| 4 | C-4 | 830.77 | 20.0 | 36.7 |
| 5 | C-6 | 886.61 | 110.0 | 32.8 |
| 6 | C-8 | 1308.34 | 75.0 | 40.7 |
| 7 | C-10 | 774.7 | 100.0 | 32.2 |
| 8 | C-12 | 886.9 | 15.0 | 35.3 |
| 9 | C-14 | 926.9 | 12.0 | 45.1 |

Transmittance Electron Microscopy (TEM)

The morphologies of the cationic compounds were analyzed by TEM (FEI Tecnai $G^2$ F20 electron microscope). Cationic compounds solution (5 microliters) were placed on a copper grid coated with carbon film and incubated for 1 minute. Phosphotungstic acid solution (0.1 w/v, 5 microliters) was applied and incubated for another minute. The extra sample on the grid was absorbed by filter paper. The samples were air-dried at room temperature. The TEM observations were carried out with an electron kinetic energy of 200 keV.

Blank Nanofiber Preparation

Cationic bis-urea compounds C-4 and C-14 formed supramolecular structures when dissolved in water above their CMCs (12 mg/L and 20 mg/L, respectively) using the following procedures.

Example 10

A blank nanofiber solution of C-4 was prepared by a membrane dialysis method. The cationic compound C-4 (10 mg) as dissolved in DMF (2 mL). The solution was then dialyzed against deionized (DI) water at room temperature (22° C.) for 24 hours using a dialysis membrane with a molecular weight cut-off of 1,000 (Spectra/Por 7, Spectrum Laboratories Inc.). The final concentration of C-4 nanofibers was 200 mg/L.

Example 11

A blank nanofiber solution of C-14 was prepared by the procedure of Example 10 having a final concentration of 80 mg/L.

C-4 and C-14 formed fine fibers (several hundred nanometers in length and ~5 nm in diameter) at concentrations of 200 mg/L and 80 mg/L, respectively. FIGS. 2A to 2C are transmission electron micrographs (TEM) of a cast film of the nanofibers formed with C-4 at different magnifications.

Atomic force microscopy (AFM) images were acquired on commercial instrumentation under fluid in intermittent contact ('tapping') mode at a 0.5 Hz scan rate with silicon on nitride cantilevers of spring constant about 0.35 N/m. For this study, images were collected over scan areas from 1×1 micrometer to 10×10 micrometers at 1024×1024 pixel resolution. Samples were prepared by depositing 60 microliters of polymer solution (at a concentration appropriate for imaging) in water on mica. The statistical mean height ($z_m$) of the nanoparticles was obtained through Gwyddion software for particle analysis using height threshold algorithm.

The dry nanofiber AFM (FIG. 3A) and solution AFM (FIGS. 3B and 3C) of nanofibers formed with C-4 show anisotropic structures having considerably shorter lengths and an average diameter of 4 nm. From the AFM analysis, the fibers had an average length of about 30 nm to about 100 nm.

The overall net charge of the fibers was determined by measuring the zeta potentials. All self-assembled bis-cationic compounds were found to have zeta potentials ranging from 21 to 30 mV (Table 2).

PenG-Loaded Nanofiber Preparation

Example 12

Penicillin G (penG) was dissolved in deionized (DI) water (10.0 mg/mL) to form a drug solution, and 35.8 microliters of this drug solution was added to blank nanofibers of C-4 (4 mL, 200 mg/L). The solution was stirred at 200 rpm for 3 hours and allowed to stand for 3 hours at room temperature.

Example 13

12.8 microliters of the penG solution prepared in Example 12 was added to blank nanofibers of C-14 (4 mL, 80 mg/L). The solution was stirred at 200 rpm for 3 hours and allowed to stand for 3 hours at room temperature.

Table 3 lists the mole ratios of the penG-loaded nanofibers.

TABLE 3

| Example | Bis-Cationic Compound | Bis-Cationic Compound (MW) | Bis-Cationic Compound (mg) | Bis-Cationic Compound (micromoles) | PenG Potassium Salt (micromoles, MW 372.5) | Bis-Cationic Compound:PenG (mole ratio) |
| --- | --- | --- | --- | --- | --- | --- |
| 12 | C-4 | 830.77 | 0.80 | 0.96 | 0.96 | 1:1 |
| 13 | C-14 | 926.9 | 0.32 | 0.35 | 0.35 | 1:1 |

The blank nanofibers sequester anionic drugs using the multivalency of the charged assembled structures without loss of the nanostructured features. FIG. 4 shows a set of TEMs of blank nanofibers of C-4 (Example 10, left image) and penG-loaded C-4 (Example 12, right image), showing that the nanofiber structure is maintained in the penG-loaded sample.

The zeta potential of cationic nanofibers before and after drug encapsulation was investigated using the drug piperacillin and C-4 and C-14. It was found that the zeta potential value of nanofibers of C-4 before and after drug loading were 35.2 and 23.1 mV, respectively. The zeta potential values of nanofibers of C-14 before and after drug loading were 36.3 and 21.1 mV, respectively. The reduced zeta potential was attributed to the electrostatic interaction between cationic nanofiber and the drug. This proves the formation of a complex between cationic nanofiber and the drug.

In Vitro Drug Release

The penG-loaded nanofiber solutions were prepared as described above. That is, in a typical example represented by Example 12, 35.8 microliters of penG solution (10.0 mg/mL) was added to blank nanofibers for in vitro drug release. The solutions (~4 mL) were transferred to dialysis membrane tubes with a molecular weight cut-off of 1000 (Spectra/Por 7, Spectrum Laboratories Inc.). The tubes were then immersed in a beaker containing 20 mL phosphate buffered saline (PBS) buffer, which was shaken with a speed of 100 rev/min. At specific time intervals, the entire PBS solution was withdrawn from the release medium and replaced with fresh PBS buffer. The penG content was then analyzed by high performance liquid chromatography (HPLC). The HPLC system consisted of a Waters 2690 separation module and Waters 996 PDA detector (Waters Corporation, USA). A Waters Symmetryshield $C_{18}$ 4.6×15.0 cm column fitted with $C_{18}$ guard column was used. The temperatures of column and samples were set at 28° C. and 15° C., respectively. The detection wavelength was set at 210 nm. A calibration curve was constructed to determine penG concentration in the range of 1 to 50 ppm (i.e., 50 mg/L) and the $r^2$ value was 0.999. The mobile phase consists of acetonitrile/0.025 M potassium phosphate (80:20 v/v) adjusted to pH 4.0 with phosphoric acid and the flow rate was set to 1 mL/min.

Figure 5:
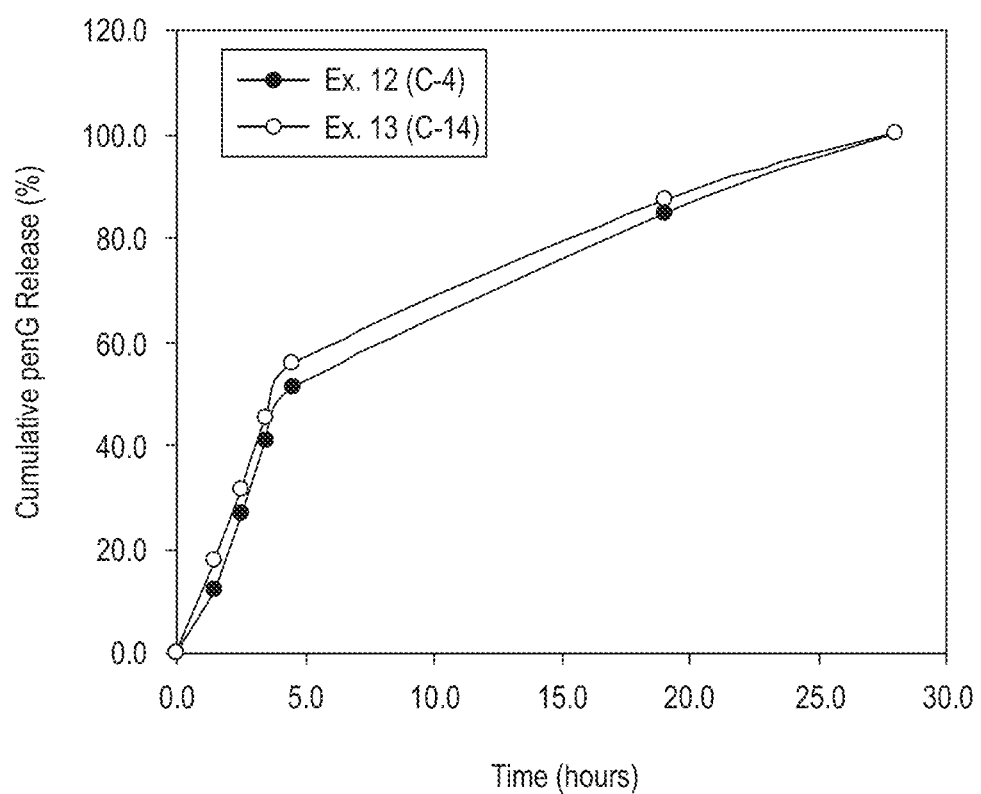
FIG. 5 is a graph showing the release rate of penG from penG loaded nanofibers of C-4 (Example 12) and penG-loaded nanofibers of C-14 (Example 13).

FIG. 5 (graph) shows that the penG release from the penG-loaded C-4 (Example 12) and penG-loaded C-14 (Example 13) fibers was sustained over 28 hours.

Antimicrobial Assays

The minimum inhibitory concentrations (MICs) of the penG-loaded nanofibers were measured using a broth microdilution method. First, penG-loaded nanofiber solutions were diluted to give final penG concentrations of 0.05, 0.1, 0.5, 1.0, 5.0 and 10.0 mg/L. S. aureus was grown in tryptic soy broth (TSB) at 37° C. with 300 rpm. The optical density (OD) of the S. aureus solution was adjusted to $OD_{600\ nm}$=0.1 by the addition of TSB. This S. aureus solution was further diluted 100 times (5.7×10$^6$ CFU/mL). The penG-loaded nanofiber solution (100 microliters) was transferred to each well of a 96 well plate (NUNC), followed by the addition of 100 microliters of the S. aureus solution. TSB was used as a control. The optical density readings of S. aureus solutions were monitored by measuring $OD_{600\ nm}$ at predetermined times (0 hours and 18 hours). The assay was performed in four replicates for each sample and the experiments were repeated at least three times.

Figure 6A:
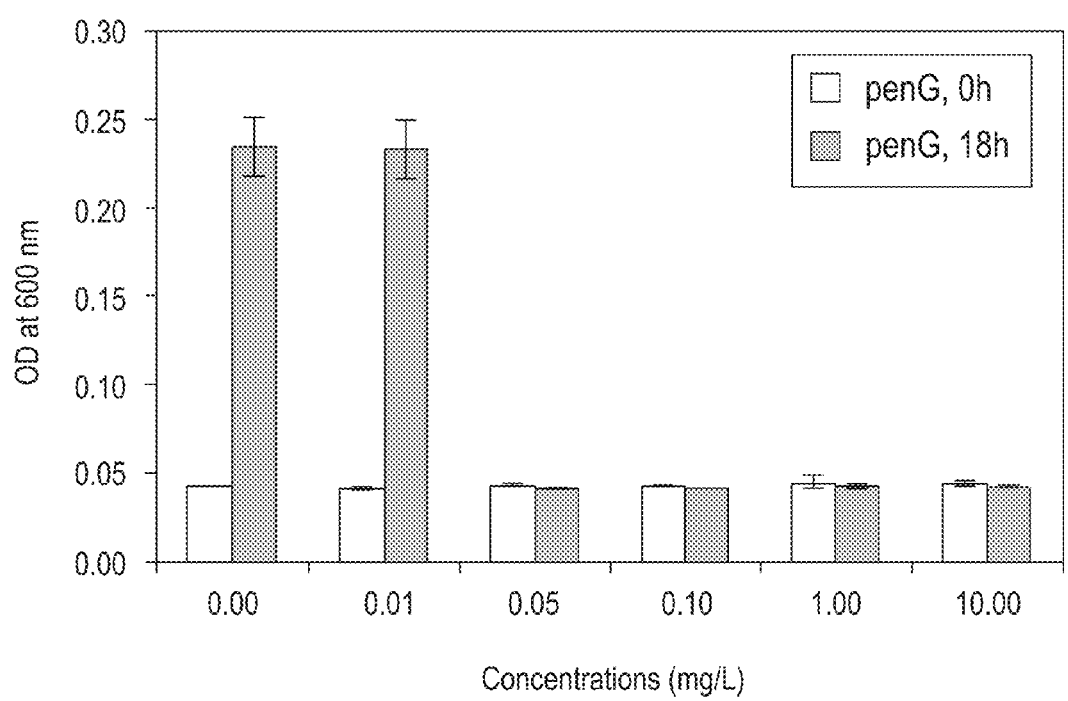
FIGS. 6A-6C are bar graphs showing dose-dependent growth inhibition of *Staphylococcus aureus* (*S. aureus*) after 0 and 18 hours incubation by penG (FIG. 6A); penG-loaded nanofibers self-assembled from compound C-4 (Example 12, FIG. 6B); and penG-loaded nanofibers formed from cationic compound C-14 (Example 13, FIG. 6C).
Figure 6B:
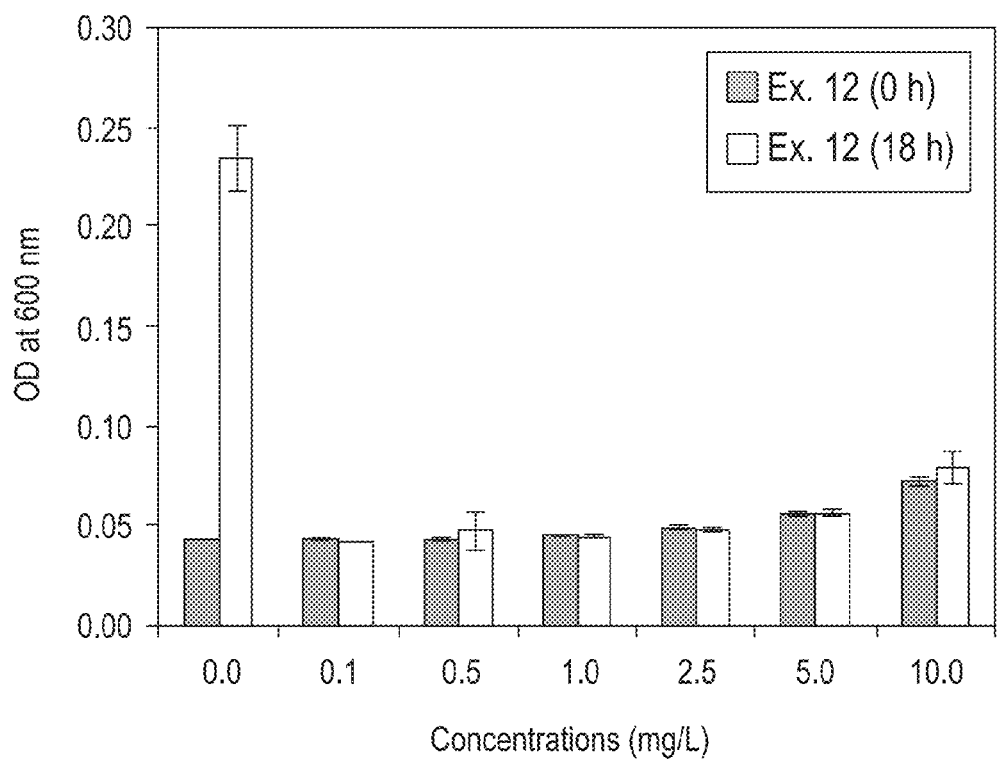
Figure 6C:
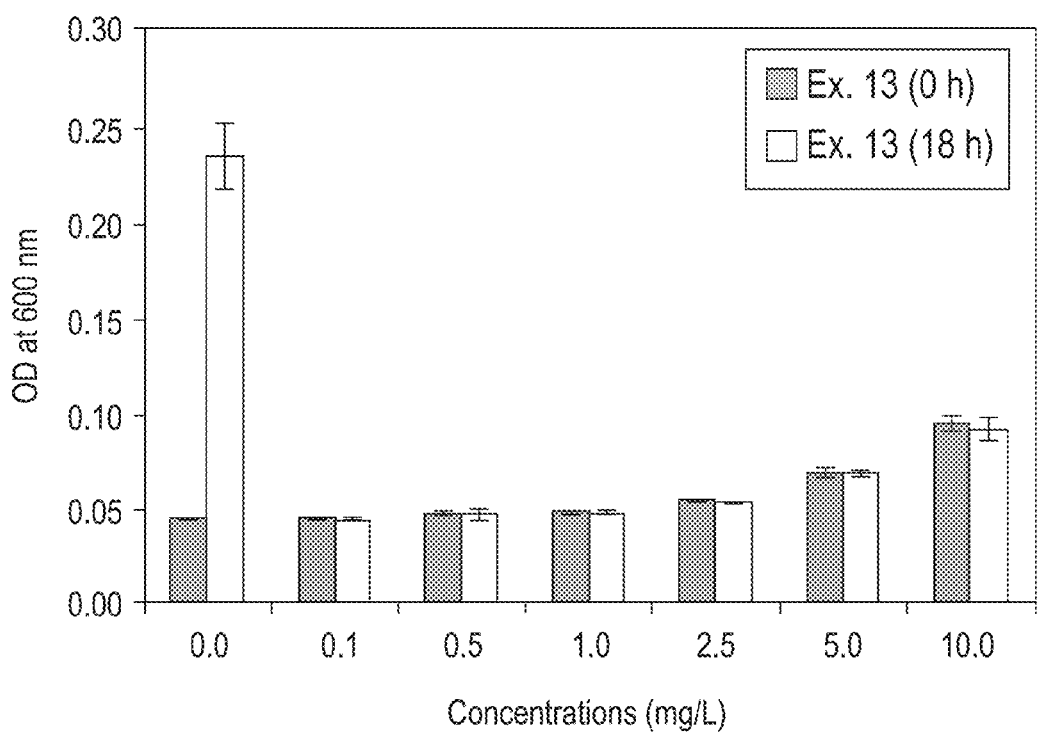

FIGS. 6A to 6C (bar graphs) compares the dose dependent growth inhibition of S. aureus by penG alone (FIG. 6A), penG-loaded C-4 (FIG. 6B, Example 12), and penG-loaded C-14 (FIG. 6C, Example 13). The released penG suppressed the growth of S. aureus as efficiently as free penG, with minimum concentrations of 0.05, 0.1, and 0.1 mg/L, respectively. The slightly increased optical density (OD) at the highest concentrations was attributed to solubility effects at higher concentrations of the drug complex.

OD measurements have shown that nanofibers of C-4 alone and C-14 alone do not inhibit growth of S. aureus.

The antimicrobial activity of penG-loaded nanofibers was further tested through a spread plate method. S. aureus was treated at 1×MIC and 2×MIC concentrations of penG-loaded nanofibers. Microbial suspensions were withdrawn after 18 hours incubation and diluted sequentially, and then plated on 1.5% LB agar plates. The plates were incubated for 24 hours at 37° C. Microbial colonies were formed and counted. The results are expressed as % kill=[(cell count of control−survivor count of sample)/cell count of control]×100. The experiments were performed in triplicate and were repeated three times.

Figure 7:
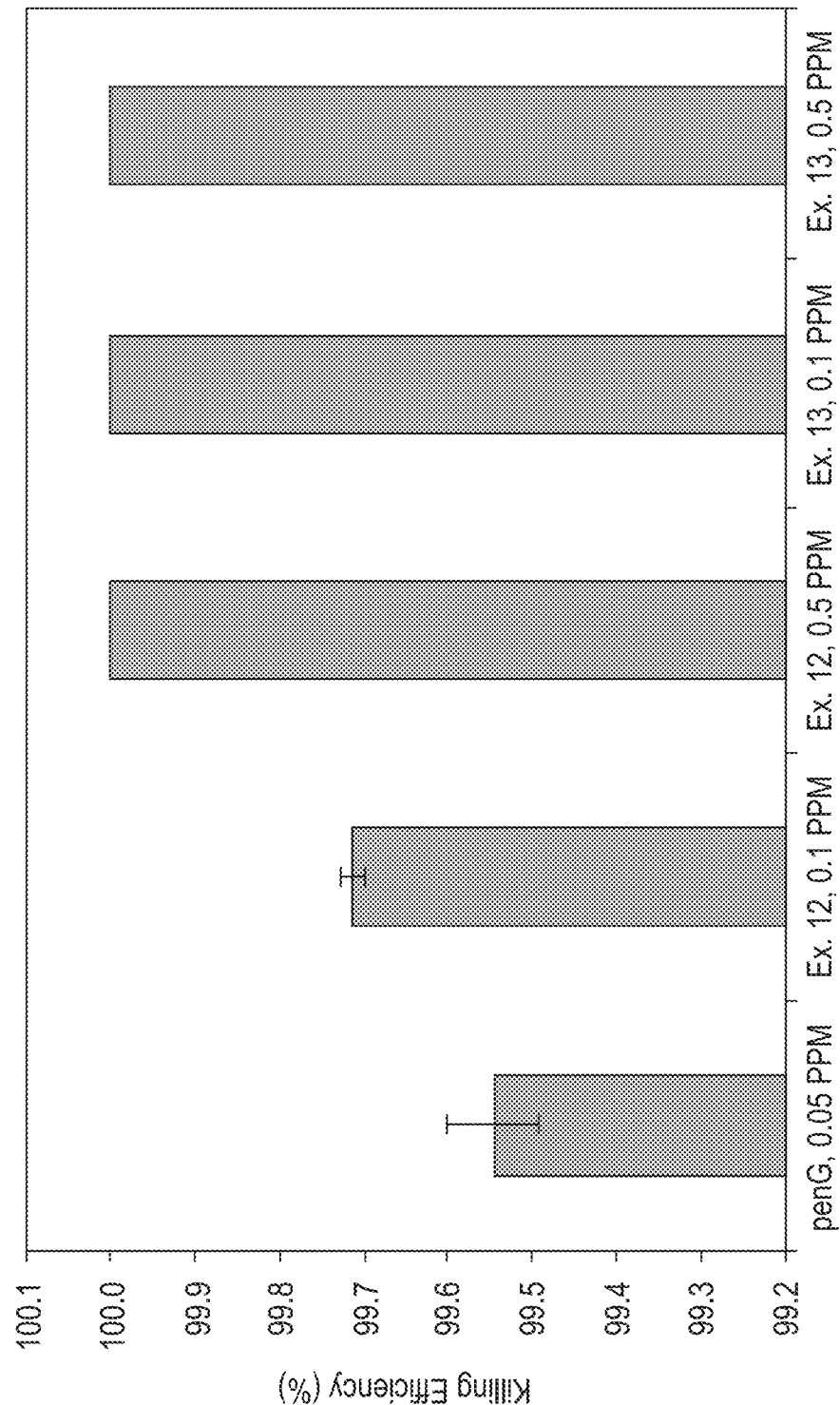
FIG. 7 is a bar graph showing the percentage of killing efficiency of various formulations against *S. aureus* after being treated at specified concentrations for 18 hours (*S. aureus* initial loading 5.7×106 CFU/mL), where ppm=mg/L.

At the minimum inhibitory concentration (MIC), penG-loaded nanofibers of C-4 (Example 12) and penG-loaded nanofibers of C-14 (Example 13) killed the bacteria more efficiently than free penG (FIG. 7, bar graph). At a concentration of 2×MIC, almost 100% of the bacteria were eradicated by penG-loaded C-4 and penG-loaded C-14 fibers.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A drug composition, comprising:
    a solvent; and
    a drug complex dispersed in the solvent, the drug complex comprising a drug selected from the group consisting of anionic forms of antimicrobial drugs, anionic forms of non-steroidal anti-inflammatory drugs (NSAIDs), and combinations thereof, the drug bound by non-covalent interactions to a fiber, wherein i) the fiber has an average diameter of 4 nm to 10 nm, ii) the fiber has an aspect ratio of 100:1 or more, iii) the fiber comprises 3 or more self-assembled molecules of a bis-urea compound bound by non-covalent interactions, and iv) the bis-urea compound has a structure according to formula (1):

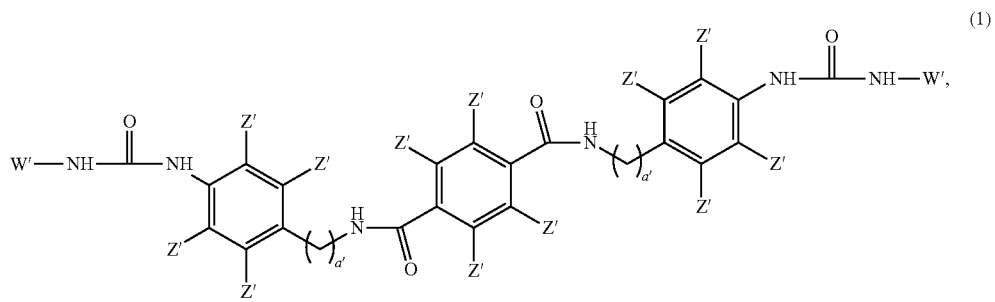

wherein
a' is 0 or 1,
each W' is an independent monovalent radical comprising a cationic group, wherein W' comprises 2 to about 25 carbons, and
each Z' is an independent monovalent radical selected from the group consisting of hydrogen, halides, and functional groups comprising 1 to about 6 carbons.

2. The drug composition of claim 1, wherein the solvent is water.

3. The drug composition of claim 1, wherein the bis-urea compound:drug mole ratio of the composition is about 1:1.

4. The drug composition of claim 1, wherein the drug composition is suitable for controlled release of the drug.

5. The drug composition of claim 1, wherein the drug is an anionic form of an antimicrobial drug.

6. The drug composition of claim 1, wherein the drug is an anionic form of a non-steroidal anti-inflammatory drug (NSAID).

7. The drug composition of claim 1, wherein the drug composition is effective in killing a microbe selected from the group consisting of Gram-negative microbes, Gram-positive microbes, fungi, yeasts, and combinations thereof.

8. A method of forming a drug composition, comprising:
    forming a first mixture comprising a solvent and a bis-urea compound of formula (1):

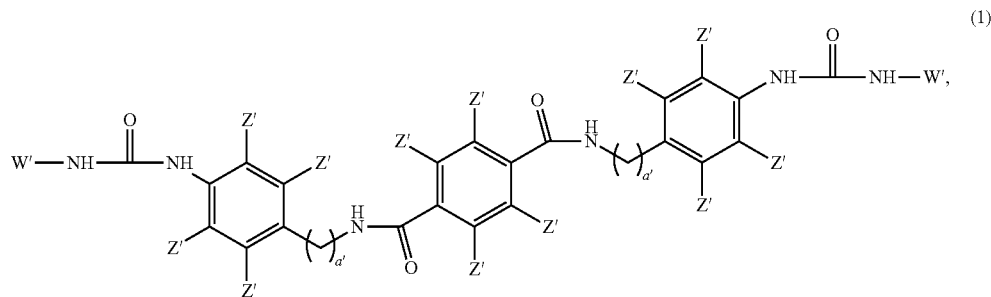
(1)

wherein
a' is 0 or 1,
each W' is an independent monovalent radical comprising a cationic group, wherein W' comprises 2 to about 25 carbons, and
each Z' is an independent monovalent radical selected from the group consisting of hydrogen, halides, and functional groups comprising 1 to about 6 carbons;
allowing the bis-urea compound of the first mixture to self-assemble, thereby forming a second mixture comprising fibers, wherein i) each of the fibers comprises 3 or more self-assembled molecules of the bis-urea compound bound by non-covalent interactions, and ii) each of the fibers has an aspect ratio of 100:1 or more and an average diameter of 4 nm to 10 nm; and adding a drug selected from the group consisting of anionic forms of antimicrobial drugs, anionic forms of non-steroidal anti-inflammatory drugs (NSAIDs), and combinations thereof, to the second mixture, thereby forming the drug composition, wherein the drug composition comprises a complex of the drug and the fibers bound by non-covalent interactions, and the drug composition is suitable for controlled release of the drug.

9. The drug composition of claim 1, wherein the bis-urea compound is selected from the group consisting of:

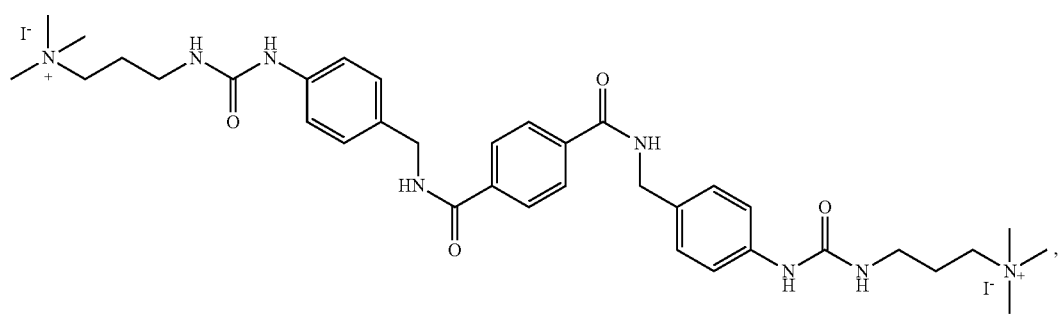
(C-2)

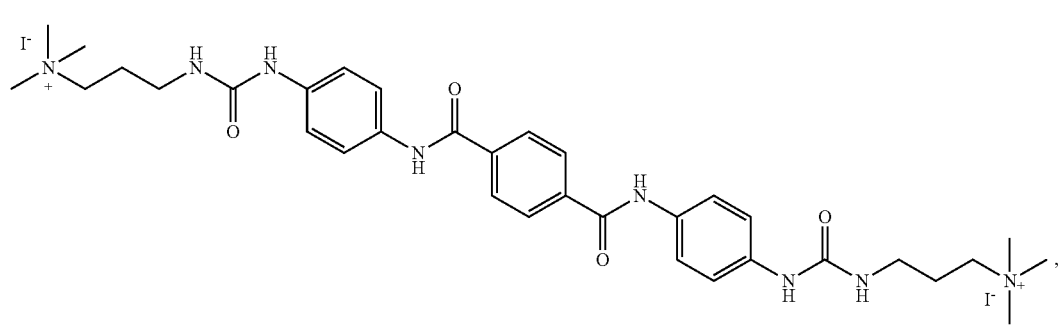
(C-4)

(C-6)
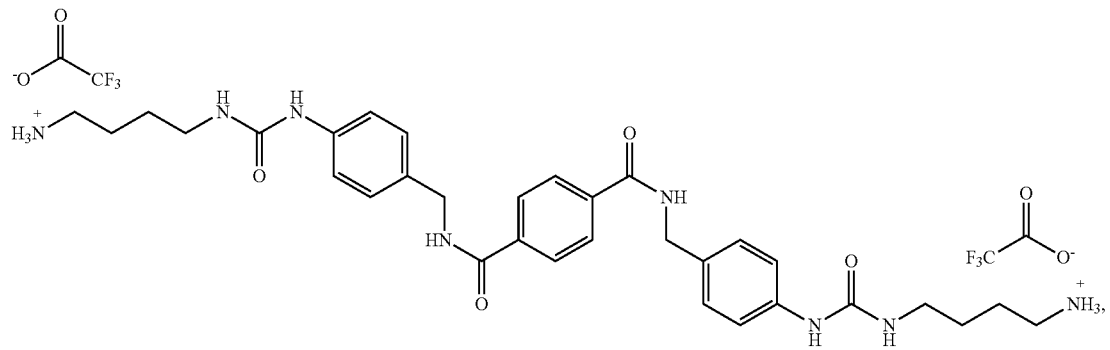
(C-8)
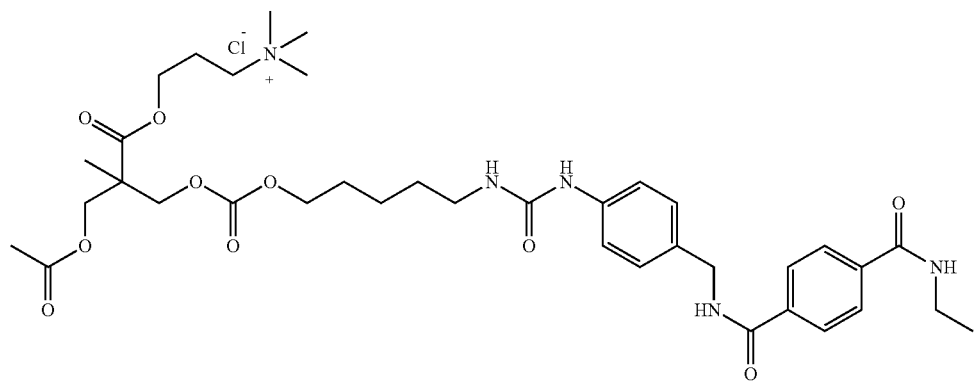
(C-10)
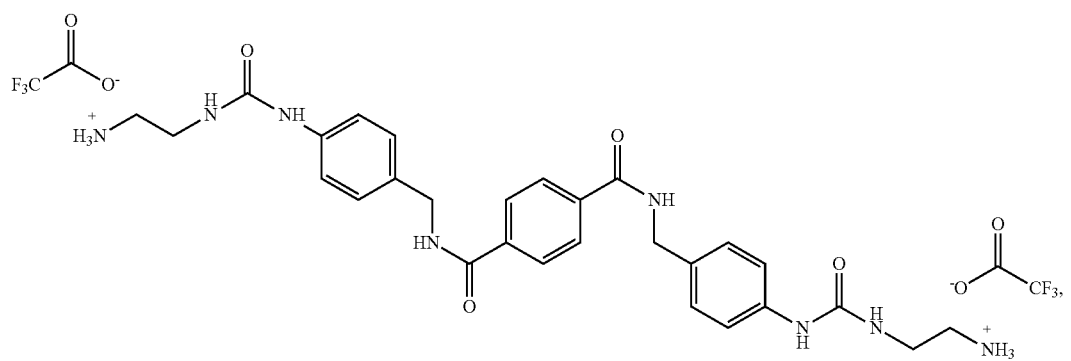

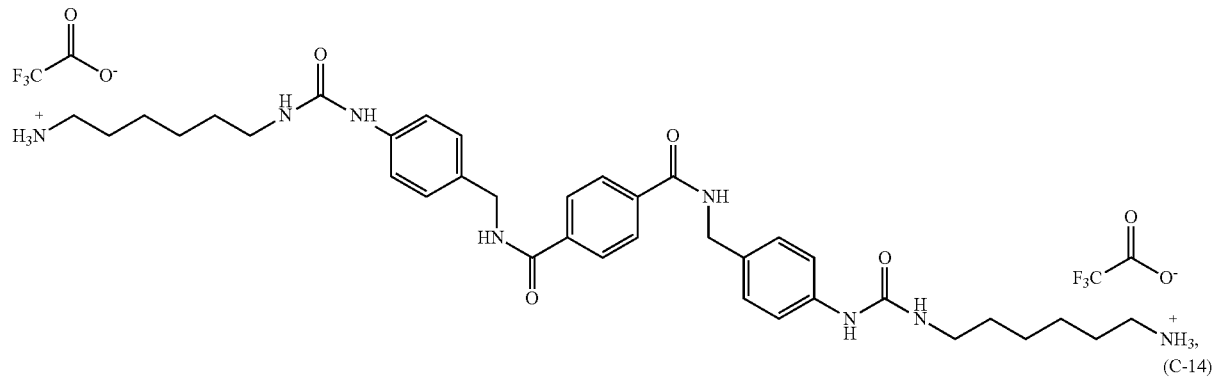
(C-12)
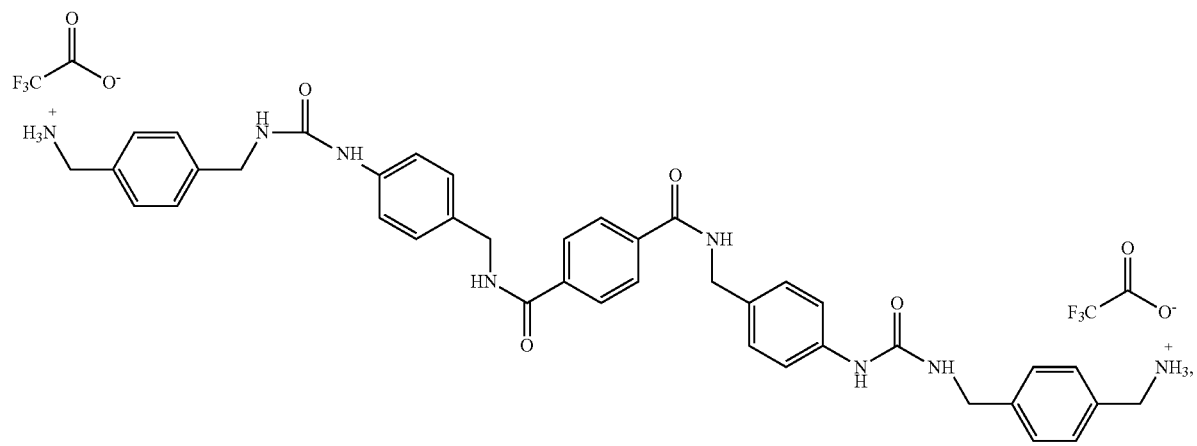
(C-14)
and combinations thereof.
10. The drug composition of claim 1, wherein the drug is an anionic form of a penicillin compound.
11. The drug composition of claim 10, wherein the penicillin compound is of formula (4):
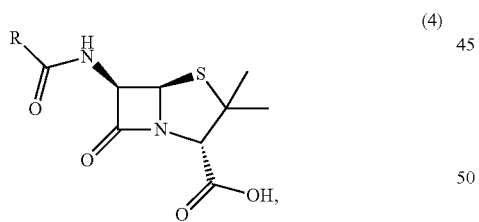
wherein R is a monovalent radical comprising 1 or more carbons.
12. The drug composition of claim 1, wherein the drug is an anionic form of penicillin G:
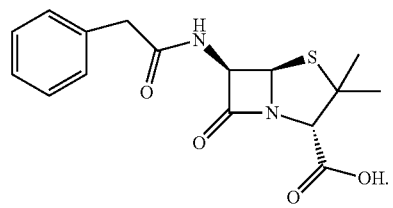 [SMILES: CC1(C)S[C@@H]2[C@H](NC(=O)Cc3ccccc3)C(=O)N2[C@H]1C(=O)O]
* * * * *